(12) United States Patent
Bradner et al.

(10) Patent No.: US 9,074,009 B2
(45) Date of Patent: Jul. 7, 2015

(54) STABILIZED MAML PEPTIDES AND USES THEREOF

(75) Inventors: James Bradner, Cambridge, MA (US); Raymond Moellering, Cambridge, MA (US); Gregory L. Verdine, Newton, MA (US)

(73) Assignees: Dana-Farber Cancer Institute, Inc., Boston, MA (US); President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 12/478,504

(22) Filed: Jun. 4, 2009

(65) Prior Publication Data

US 2010/0081611 A1    Apr. 1, 2010

Related U.S. Application Data

(63) Continuation of application No. PCT/US2007/084838, filed on Nov. 15, 2007.

(60) Provisional application No. 60/859,379, filed on Nov. 15, 2006.

(51) Int. Cl.
  *C07K 7/00*  (2006.01)
  *A61K 38/00*  (2006.01)
  *C07K 14/47*  (2006.01)

(52) U.S. Cl.
  CPC ........ *C07K 14/47* (2013.01); *A61K 38/00* (2013.01)

(58) Field of Classification Search
  None
  See application file for complete search history.

(56) References Cited

U.S. PATENT DOCUMENTS

| | | | |
|---|---|---|---|
| 5,811,515 A | 9/1998 | Grubbs et al. | |
| 5,851,775 A | 12/1998 | Barker et al. | |
| 6,031,072 A | 2/2000 | Blaschuck et al. | |
| 7,192,713 B1* | 3/2007 | Verdine et al. | 435/7.1 |
| 7,202,332 B2 | 4/2007 | Arora et al. | |
| 7,214,488 B2* | 5/2007 | Kaye et al. | 435/6.14 |
| 7,705,118 B2 | 4/2010 | Arora et al. | |
| 7,723,469 B2* | 5/2010 | Walensky et al. | 530/317 |
| 7,786,072 B2* | 8/2010 | Verdine et al. | 514/21.4 |
| 7,838,711 B2* | 11/2010 | Herweck et al. | 585/645 |
| 7,875,601 B2* | 1/2011 | O'Reilly et al. | 514/183 |
| 7,960,506 B2 | 6/2011 | Nash | |
| 7,981,998 B2 | 7/2011 | Nash | |
| 7,981,999 B2 | 7/2011 | Nash | |
| 2005/0250680 A1* | 11/2005 | Walensky et al. | 514/9 |
| 2006/0008848 A1 | 1/2006 | Verdine et al. | |
| 2007/0117154 A1 | 5/2007 | Deslongchamps et al. | |
| 2007/0203057 A1 | 8/2007 | Dhoerty et al. | |
| 2008/0081831 A1 | 4/2008 | Gour et al. | |
| 2008/0262200 A1 | 10/2008 | Nash | |
| 2009/0149630 A1 | 6/2009 | Walensky et al. | |
| 2009/0176964 A1 | 7/2009 | Walensky et al. | |
| 2009/0275519 A1 | 11/2009 | Nash et al. | |
| 2009/0326192 A1 | 12/2009 | Nash et al. | |
| 2010/0184628 A1 | 7/2010 | Nash | |
| 2010/0234563 A1 | 9/2010 | Arora et al. | |
| 2011/0028753 A1 | 2/2011 | Verdine et al. | |
| 2011/0046043 A1 | 2/2011 | Wang et al. | |
| 2011/0144303 A1 | 6/2011 | Nash et al. | |
| 2011/0245175 A1 | 10/2011 | Arora et al. | |
| 2011/0263815 A1 | 10/2011 | Nash | |
| 2012/0190818 A1 | 7/2012 | Nash et al. | |

FOREIGN PATENT DOCUMENTS

| | | |
|---|---|---|
| WO | WO 93/19176 A1 | 9/1993 |
| WO | WO2005/0044839 | 5/2005 |
| WO | WO 2005/044839 A3 | 7/2005 |
| WO | WO 2006/038208 A2 | 4/2006 |
| WO | WO 2006/038208 A3 | 5/2007 |
| WO | WO 2008/061192 A2 | 5/2008 |
| WO | WO 2008/076904 A1 | 6/2008 |
| WO | WO 2008/061192 A3 | 7/2008 |
| WO | WO 2008/104000 A2 | 8/2008 |
| WO | WO 2008/121767 A2 | 10/2008 |
| WO | WO 2008/104000 A3 | 11/2008 |
| WO | WO 2008/121767 A3 | 1/2009 |
| WO | WO 2009/099677 A2 | 8/2009 |
| WO | WO 2009/099677 A3 | 12/2009 |

OTHER PUBLICATIONS

Wu et. al. Modulation of Notch Signaling by Mastermind-like(MAML) transcriptional co-activators and their involvement in tumerogenesis, Seminars in Cancer Biology 14, 348-356, (2004).*
Wu et. al. Modulation of Notch Signaling by Mastermind-like(MAML) transcriptional co-activators and their involvement in tumerogenesis, Seminars in Cancer Biology 14, 348-356, 2004.*
Nam et. al. Structural Basis for Cooperativity in Recruitment of MAML Coactivators to Notch Transcription Complexes, Cell 124, 973-983, Mar. 10, 2006.*
Maillard et. al. Mastermind critically regulates Notch-mediated lymphoid cell fate decisions, Blood, 2004 104: 1696-1702, Jun. 8, 2004. bloodjournal.hematologylibrary.org.*
Walensky L D et al., "Activation of Apoptosis in Vivo by a Hydrocarbon-Stapled BH3 Helix", Science, 305: 1466-1472 (2004).
Nam Yunsun et al., "Structural Basis for Cooperativity in Recruitment of MAML Coactivators to Notch Transcription Complexes", Cell 124:973-983 (2006).
Phelen J C et al., "A General Method for Constraining Short Peptides to an Aspire-Helical Conformation", Journal of the American Chemical Society, 119:455-460 (1997).
European search report and search opinion dated Dec. 7, 2009 for EP Application No. 07871487.
International search report and written opinion dated May 16, 2008 for PCT Application No. US2007/084838.
Nam, et al. Structural basis for cooperativity in recruitment of MAML coactivators to Notch transcription complexes. Cell. Mar. 10, 2006; 124(5):973-83.
Schafmeister, et al. An All-Hydrocarbon Cross-Linking System for Enhancing the Helicity and Metabolic Stability of Peptides, J. Am. Chem. Soc., 2000, 122 (24), pp. 5891-5892.

(Continued)

*Primary Examiner* — James H Alstrum Acevedo
*Assistant Examiner* — Jeanette Lieb
(74) *Attorney, Agent, or Firm* — Fish & Richardson P.C.

(57) ABSTRACT

Stably cross-linked a polypeptides related to human MAML are described. These cross-linked polypeptides contain at least two modified amino acids that together form an internal cross-link or tether that can help to stabilize the alpha-helical secondary structure that is thought to be important for binding of MAML peptides to the Notch transcription complex, a complex that includes ICN and CSL.

12 Claims, 23 Drawing Sheets

(56) References Cited

OTHER PUBLICATIONS

U.S. Appl. No. 13/120,360, filed Mar. 22, 2011, Nash et al.
U.S. Appl. No. 13/120,370, filed Mar. 22, 2011, Nash et al.
U.S. Appl. No. 13/120,376, filed Mar. 22, 2011, Nash et al.
U.S. Appl. No. 13/120,386, filed Mar. 22, 2011, Nash et al.
U.S. Appl. No. 13/129,118, filed Nov. 1, 2011, Nash et al.
U.S. Appl. No. 13/250,344, filed Sep. 30, 2011, Arora et al.
U.S. Appl. No. 13/252,751, filed Oct. 4, 2011, Walensky et al.
U.S. Appl. No. 13/366,113, filed Feb. 3, 2012, Nash et al.
Erez, et al. Induction of apoptosis in cultured endothelial cells by a cadherin antagonist peptide: involvement of fibroblast growth factor receptor-mediated signalling. Exp Cell Res. Apr. 1, 2004;294(2):366-78. Abstract only.
Freedman, et al. Structural basis for recruitment of CBP/p300 by hypoxia-inducible factor-1 alpha. Proc Natl Acad Sci U S A. Apr. 16, 2002; 99(8):5367-72
Ghanem, et al. Peptide-mediated interference with influenza A virus polymerase. J Virol. Jul. 2007; 81(14):7801-4.
Giorello, et al. Inhibition of cancer cell growth and c-Myc transcriptional activity by a c-Myc helix 1-type peptide fused to an internalization sequence. Cancer Res. Aug. 15, 1998;58(16):3654-9.
International search report and written opinion dated Jan. 7, 2011 for PCT Application No. US2010/049892.
International search report and written opinion dated Feb. 16, 2010 for PCT Application No. US2009/057927.
International search report and written opinion dated Mar. 5, 2010 for PCT Application No. US2009/057928.
International search report and written opinion dated Mar. 8, 2010 for PCT Application No. US09/057925.
International search report and written opinion dated Mar. 10, 2010 for PCT Application No. US2009/057930.
International search report and written opinion dated Jul. 6, 2010 for PCT Application No. US2010/021091.
Latini, et al. 395 Blocking the interaction between HIF-1alpha and p300 by a 32 amino acid fragment of p35srj inhibits the hypoxia induced transcriptional activity of HIF-1alpha in human U87MG glioma cells. Euro J Canc Suppl. 2004; 2(8):118.
Moellering, et al. Direct inhibition of the NOTCH transcription factor complex. Nature. Nov. 12, 2009;462(7270):182-8.
Rankin, et al. The role of hypoxia-inducible factors in tumorigenesis. Cell Death Differ. Apr. 2008;15(4):678-85.
Rushe, et al. Structure of a NEMO/IKK-associating domain reveals architecture of the interaction site. Structure. May 2008;16(5):798-808.
Williams, et al. A novel family of cyclic peptide antagonists suggests that N-cadherin specificity is determined by amino acids that flank the HAV motif. J Biol Chem. Feb. 11, 2000;275(6):4007-12.
Williams, et al. Dimeric versions of two short N-cadherin binding motifs (HAVDI and INPISG)function as N-cadherin agonists. J Biol Chem. Feb. 8, 2002;277(6):4361-7.
Office action dated Nov. 8, 2012 for U.S. Appl. No. 13/120,386.
Maillard, et al., Mastermind critically regulates Notch-mediated lymphoid cell fate decisions. *Blood.* Sep. 15, 2004;104(6):1696-702. Epub Jun. 8, 2004.
Weng, et al., Growth Suppression of Pre-T Acute Lymphoblastic Leukemia Cells by Inhibition of Notch Signaling. *Mol Cell Biol.* Jan. 2003;23(2):655-64.

* cited by examiner

```
           1111111222222222233333333334444444444555555555566666666667777
           34567890123456789012345678901234567890123456789012345678901234

MAML-1     1prHSAVMERLRRRIELCRRHHSTCEARYEAVspERLELERQHTFALHQRCIQAKAKRagkh
HELICAL    1prHSAVMERLRRRIELCRRHHSTCEARYEAVspERLELERQHTFALHQRCIQAKAKRagkh
Cons.Abs   1prHSAVMERLRRRIELCRRHHSTCEARYEAVspERLELERQHTFALHQRCIQAKAKRagkh
Cons.Hum   1prHSAVMERLRRRIELCRRHHSTCEARYEAVspERLELERQHTFALHQRCIQAKAKRagkh
ANK        1prHSAVMERLRRRIELCRRHHSTCEARYEAVspERLELERQHTFALHQRCIQAKAKRagkh
ANK.CSL    1prHSAVMERLRRRIELCRRHHSTCEARYEAVspERLELERQHTFALHQRCIQAKAKRagkh
Phase1     1prHSAVMERLRRRIELCRRHHSTCEARYEAVspERLELERQHTFALHQRCIQAKAKRagkh
Phase2     1prHSAVMERLRRRIELCRRHHSTCEARYEAVspERLELERQHTFALHQRCIQAKAKRagkh
Phase3     1prHSAVMERLRRRIELCRRHHSTCEARYEAVspERLELERQHTFALHQRCIQAKAKRagkh
Phase4     1prHSAVMERLRRRIELCRRHHSTCEARYEAVspERLELERQHTFALHQRCIQAKAKRagkh
Phase5     1prHSAVMERLRRRIELCRRHHSTCEARYEAVspERLELERQHTFALHQRCIQAKAKRagkh
Phase6     1prHSAVMERLRRRIELCRRHHSTCEARYEAVspERLELERQHTFALHQRCIQAKAKRagkh
```

FIG. 1

```
         1111111222222222233333333334444444444555555555566666666667777777
         3456789012345678901234567890123456789012345678901234567890123456789012345678901234
MAML-1   1prHSAVMERLRRRIELCRRHHSTCEARYEAVspERLELERQHTFALHQRCIQAKAKRagkh
ANK.CSL  1prHSAVMERLRRRIELCRRHHSTCEARYEAVspERLELERQHTFALHQRCIQAKAKRagkh
REM-G1   1prHSAVMERLRRRIXLCRXHHSTCEARYEAVspERLELERQHTFALHQRCIQAKAKRagkh
REM-G2   1prHSAVMERLRRRIXLSRXHHSTCEARYEAVspERLELERQHTFALHQRCIQAKAKRagkh
REM-G3   1prHSAVMERLRRRIXLARXHHSTCEARYEAVspERLELERQHTFALHQRCIQAKAKRagkh
REM-G4   1prHSAVMERLRRRIXLSRRHHXTCEARYEAVspERLELERQHTFALHQRCIQAKAKRagkh
REM-G5   1prHSAVMERLRRRIXLARRHHXTCEARYEAVspERLELERQHTFALHQRCIQAKAKRagkh
REM-G6   1prHSAVMERLRRRIELCRRHHSTCEARYEAVspERLELERXHTFXLHQRCIQAKAKRagkh
REM-G7   1prHSAVMERLRRRIELCRRHHSTCEARYEAVspERLELERXHTFALHXRCIQAKAKRagkh
REM-G8   1prHSAVMERLRRRIELCRRHHSTCEARYEAVspERLELERXHTAALHXRCIQAKAKRagkh
REM-G9   1prHSAVMERLRRRIXLARRHHXTAEARYEAVspERLELERQHTFALHQRCIQAKAKRagkh
REM-G10  1prHSAVMERLXRRIXLARRHHXTAEXRYEAVspERLELERQHTFALHQRCIQAKAKRagkh
REM-G11  1prHSAVMERLRRRIELCRRHHXTCEXRYEAVspERLELERXHTFALHQRCIQAKAKRagkh
REM-G13  1prHSAVMERLRRRIELCRRHHSTCEARYEAVspERLELERXHTFXLHQRCIQAKAKRagkh
```

FIG. 3

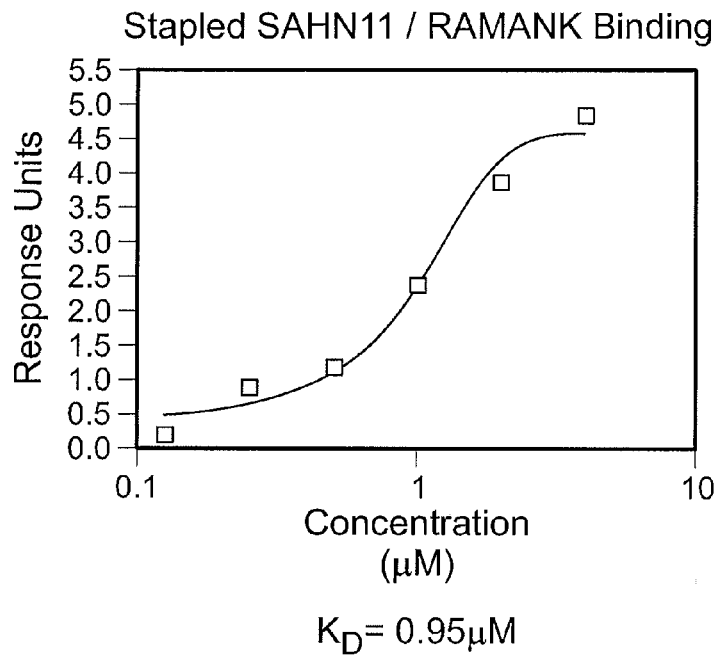
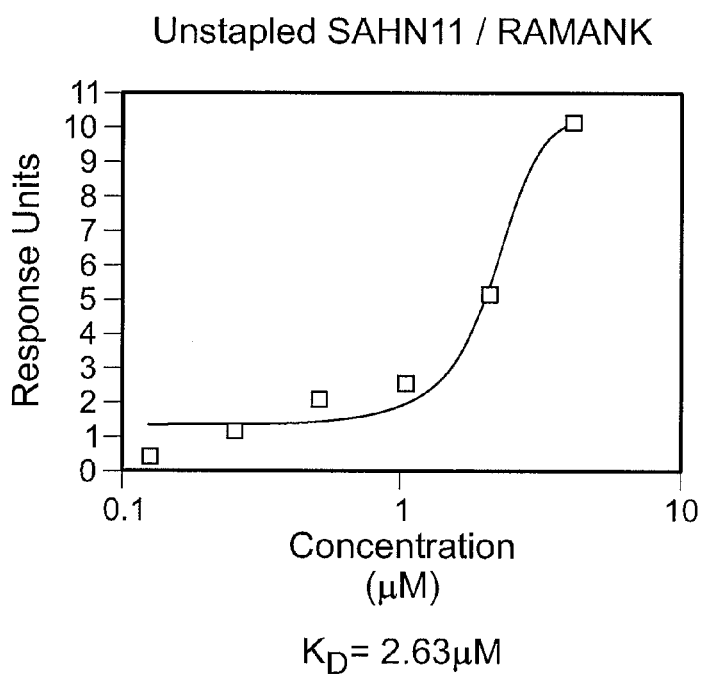
FIG. 9

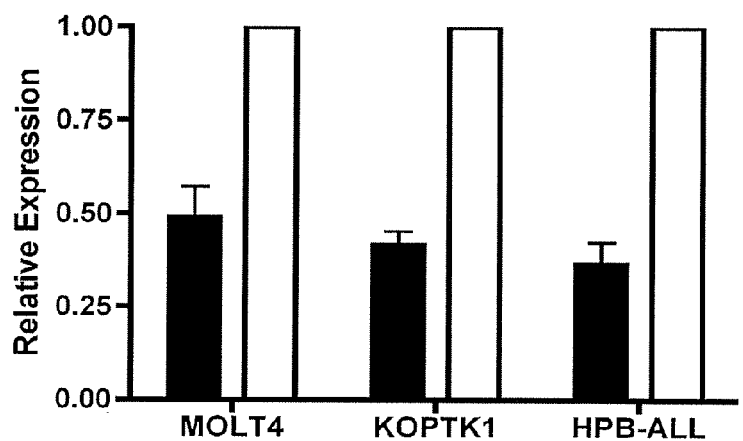
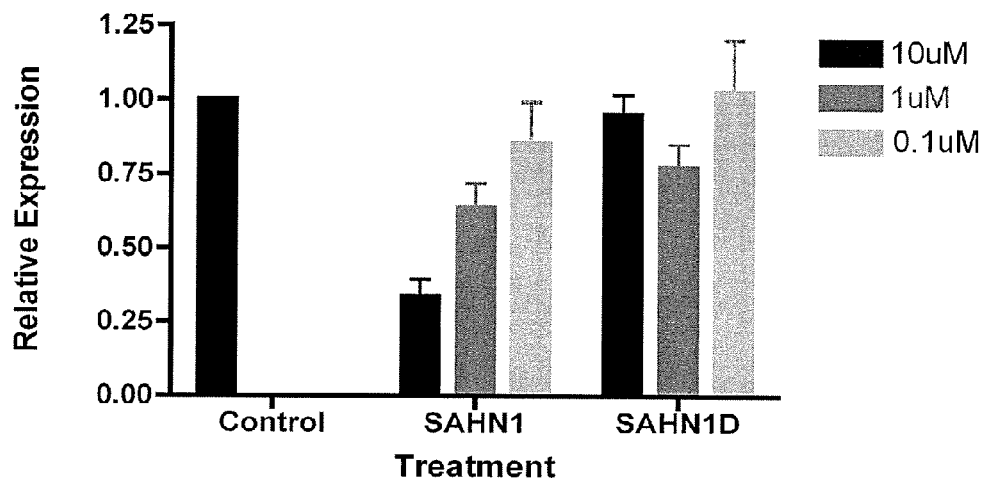
FIG. 23

Treatment:     DMSO    SAHN1   SAHN1-D
Incubation(hr):  24 | 48   24 | 48   24 | 48
Cleaved
PARP(D214)
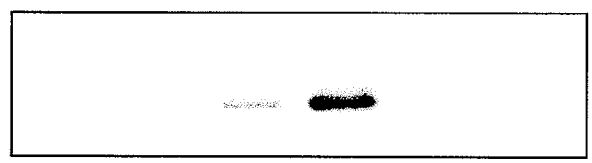
β–Actin
FIG. 24

SEQUENCE LISTING

```
<160> NUMBER OF SEQ ID NOS: 44

<210> SEQ ID NO 1
<211> LENGTH: 47
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (3)..(3)
<223> OTHER INFORMATION: Ala or Thr
<220> FEATURE:
<221> NAME/KEY: MOD_RES
<222> LOCATION: (4)..(4)
<223> OTHER INFORMATION: Val or Ile
<220> FEATURE:
<221> NAME/KEY: MOD_RES
<222> LOCATION: (5)..(5)
<223> OTHER INFORMATION: Met or Val
<220> FEATURE:
<221> NAME/KEY: MOD_RES
<222> LOCATION: (10)..(10)
<223> OTHER INFORMATION: Arg, Ala or Gln
<220> FEATURE:
<221> NAME/KEY: MOD_RES
<222> LOCATION: (11)..(11)
<223> OTHER INFORMATION: Any amino acid
<220> FEATURE:
<221> NAME/KEY: MOD_RES
<222> LOCATION: (13)..(13)
<223> OTHER INFORMATION: Glu or Ala
```

```
<220> FEATURE:
<221> NAME/KEY: MOD_RES
<222> LOCATION: (14)..(14)
<223> OTHER INFORMATION: Leu, Val or Gly
<220> FEATURE:
<221> NAME/KEY: MOD_RES
<222> LOCATION: (17)..(17)
<223> OTHER INFORMATION: Arg or Gln
<220> FEATURE:
<221> NAME/KEY: MOD_RES
<222> LOCATION: (20)..(20)
<223> OTHER INFORMATION: Ser, Leu or Val
<220> FEATURE:
<221> NAME/KEY: MOD_RES
<222> LOCATION: (21)..(21)
<223> OTHER INFORMATION: Thr, Ser or Asn
<220> FEATURE:
<221> NAME/KEY: MOD_RES
<222> LOCATION: (24)..(24)
<223> OTHER INFORMATION: Arg, Gly or Asn
<220> FEATURE:
<221> NAME/KEY: MOD_RES
<222> LOCATION: (27)..(27)
<223> OTHER INFORMATION: Glu or Gln
<220> FEATURE:
<221> NAME/KEY: MOD_RES
<222> LOCATION: (28)..(28)
<223> OTHER INFORMATION: Ala, Arg or Gln
<220> FEATURE:
<221> NAME/KEY: MOD_RES
<222> LOCATION: (29)..(29)
<223> OTHER INFORMATION: Val, Gly or Ala
<220> FEATURE:
<221> NAME/KEY: MOD_RES
<222> LOCATION: (30)..(30)
<223> OTHER INFORMATION: Ser, Arg or Gln
<220> FEATURE:
<221> NAME/KEY: MOD_RES
<222> LOCATION: (31)..(31)
<223> OTHER INFORMATION: Pro, Ala or Val
<220> FEATURE:
<221> NAME/KEY: MOD_RES
<222> LOCATION: (33)..(33)
<223> OTHER INFORMATION: Arg, Ser or Gln
<220> FEATURE:
<221> NAME/KEY: MOD_RES
<222> LOCATION: (34)..(34)
<223> OTHER INFORMATION: Leu or Ser
<220> FEATURE:
<221> NAME/KEY: MOD_RES
<222> LOCATION: (35)..(35)
<223> OTHER INFORMATION: Glu or Asp
<220> FEATURE:
<221> NAME/KEY: MOD_RES
<222> LOCATION: (36)..(36)
<223> OTHER INFORMATION: Leu or Arg
<220> FEATURE:
<221> NAME/KEY: MOD_RES
<222> LOCATION: (39)..(39)
<223> OTHER INFORMATION: Gln, Glu or Arg
<220> FEATURE:
<221> NAME/KEY: MOD_RES
<222> LOCATION: (40)..(40)
<223> OTHER INFORMATION: His, Ser or Asp
<220> FEATURE:
<221> NAME/KEY: MOD_RES
<222> LOCATION: (42)..(42)
<223> OTHER INFORMATION: Phe, Leu or Val
<220> FEATURE:
<221> NAME/KEY: MOD_RES
<222> LOCATION: (43)..(43)
<223> OTHER INFORMATION: Ala, Gln or Ser
<220> FEATURE:
<221> NAME/KEY: MOD_RES
<222> LOCATION: (45)..(45)
<223> OTHER INFORMATION: His, Leu or Tyr
<220> FEATURE:
<221> NAME/KEY: MOD_RES
<222> LOCATION: (46)..(46)
```

```
<223> OTHER INFORMATION: Gln or Ser
<220> FEATURE:
<221> NAME/KEY: MOD_RES
<222> LOCATION: (47)..(47)
<223> OTHER INFORMATION: Arg or Leu
<220> FEATURE:
<223> OTHER INFORMATION: Within SEQ ID NO:1, the following pairs of
      amino acid can be cross-linked: 2/9, 6/13, 13/17, 17/20, 20/27,
      20/24, 35/39, 39/46, and 39/43.  The corresponding residues in SEQ
      ID NOs: 2-8 can be cross-linked.

<400> SEQUENCE: 1

His Ser Xaa Xaa Xaa Glu Arg Leu Arg Xaa Xaa Ile Xaa Xaa Cys Arg
1               5                   10                  15

Xaa His His Xaa Xaa Cys Glu Xaa Arg Tyr Xaa Xaa Xaa Xaa Xaa Glu
            20                  25                  30

Xaa Xaa Xaa Xaa Glu Arg Xaa Xaa Thr Xaa Xaa Leu Xaa Xaa Xaa
        35                  40                  45

<210> SEQ ID NO 2
<211> LENGTH: 44
<212> TYPE: PRT
<213> ORGANISM: Homo sapiens
<220> FEATURE:
<223> OTHER INFORMATION: Wherein pairs of amino acid corresponding to
      amino acids 2/9, 6/13, 13/17, 17/20, 20/27, 20/24, 35/39, 39/46,
      and 39/43 shown in SEQ ID NO: 1 can be cross-linked.

<400> SEQUENCE: 2

Val Met Glu Arg Leu Arg Arg Arg Ile Glu Leu Cys Arg Arg His His
1               5                   10                  15

Ser Thr Cys Glu Ala Arg Tyr Glu Ala Val Ser Pro Glu Arg Leu Glu
            20                  25                  30

Leu Glu Arg Gln His Thr Phe Ala Leu His Gln Arg
        35                  40

<210> SEQ ID NO 3
<211> LENGTH: 44
<212> TYPE: PRT
<213> ORGANISM: Homo sapiens
<220> FEATURE:
<223> OTHER INFORMATION: Wherein pairs of amino acid corresponding to
      amino acids 2/9, 6/13, 13/17, 17/20, 20/27, 20/24, 35/39, 39/46,
      and 39/43 shown in SEQ ID NO: 1 can be cross-linked.

<400> SEQUENCE: 3

Ile Val Glu Arg Leu Arg Ala Arg Ile Ala Val Cys Arg Gln His His
1               5                   10                  15

Leu Ser Cys Glu Gly Arg Tyr Glu Arg Gly Arg Ala Glu Ser Ser Asp
            20                  25                  30

Arg Glu Arg Glu Ser Thr Leu Gln Leu Leu Ser Leu
        35                  40

<210> SEQ ID NO 4
<211> LENGTH: 44
<212> TYPE: PRT
<213> ORGANISM: Homo sapiens
<220> FEATURE:
<223> OTHER INFORMATION: Wherein pairs of amino acid corresponding to
      amino acids 2/9, 6/13, 13/17, 17/20, 20/27, 20/24, 35/39, 39/46,
      and 39/43 shown in SEQ ID NO: 1 can be cross-linked.

<400> SEQUENCE: 4

Val Val Glu Arg Leu Arg Gln Arg Ile Glu Gly Cys Arg Arg His His
1               5                   10                  15
```

Val Asn Cys Glu Asn Arg Tyr Gln Gln Ala Gln Val Glu Gln Leu Glu
                20                  25                  30

Leu Glu Arg Arg Asp Thr Val Ser Leu Tyr Gln Arg
        35                  40

<210> SEQ ID NO 5
<211> LENGTH: 59
<212> TYPE: PRT
<213> ORGANISM: Homo sapiens
<220> FEATURE:
<223> OTHER INFORMATION: Wherein pairs of amino acid corresponding to
      amino acids 2/9, 6/13, 13/17, 17/20, 20/27, 20/24, 35/39, 39/46,
      and 39/43 shown in SEQ ID NO: 1 can be cross-linked.

<400> SEQUENCE: 5

His Ser Ala Val Met Glu Arg Leu Arg Arg Arg Ile Glu Leu Cys Arg
1               5                   10                  15

Arg His His Ser Thr Cys Glu Ala Arg Tyr Glu Ala Val Ser Pro Glu
                20                  25                  30

Arg Leu Glu Leu Glu Arg Gln His Thr Phe Ala Leu His Gln Arg Cys
            35                  40                  45

Ile Gln Ala Lys Ala Lys Arg Ala Gly Lys His
        50                  55

<210> SEQ ID NO 6
<211> LENGTH: 60
<212> TYPE: PRT
<213> ORGANISM: Homo sapiens
<220> FEATURE:
<223> OTHER INFORMATION: Wherein pairs of amino acid corresponding to
      amino acids 2/9, 6/13, 13/17, 17/20, 20/27, 20/24, 35/39, 39/46,
      and 39/43 shown in SEQ ID NO: 1 can be cross-linked.

<400> SEQUENCE: 6

His Ser Ala Ile Val Glu Arg Leu Arg Ala Arg Ile Ala Val Cys Arg
1               5                   10                  15

Gln His His Leu Ser Cys Glu Gly Arg Tyr Gln Arg Gly Arg Ala Glu
                20                  25                  30

Ser Ser Asp Arg Glu Arg Glu Ser Thr Leu Gln Leu Leu Ser Leu Val
            35                  40                  45

Gln His Gly Gln Gly Ala Arg Lys Ala Gly Lys His
        50                  55                  60

<210> SEQ ID NO 7
<211> LENGTH: 60
<212> TYPE: PRT
<213> ORGANISM: Homo sapiens
<220> FEATURE:
<223> OTHER INFORMATION: Wherein pairs of amino acid corresponding to
      amino acids 2/9, 6/13, 13/17, 17/20, 20/27, 20/24, 35/39, 39/46,
      and 39/43 shown in SEQ ID NO: 1 can be cross-linked.

<400> SEQUENCE: 7

Ala Val Pro Lys His Ser Thr Val Val Glu Arg Leu Arg Gln Arg Ile
1               5                   10                  15

Glu Gly Cys Arg Arg His His Val Asn Cys Glu Asn Arg Tyr Gln Gln
                20                  25                  30

Ala Gln Val Glu Gln Leu Glu Leu Glu Arg Arg Asp Thr Val Ser Leu
            35                  40                  45

Tyr Gln Arg Thr Leu Glu Gln Arg Ala Lys Lys Ser
        50                  55                  60

```
<210> SEQ ID NO 8
<211> LENGTH: 16
<212> TYPE: PRT
<213> ORGANISM: Homo sapiens
<220> FEATURE:
<223> OTHER INFORMATION: Wherein pairs of amino acid corresponding to
      amino acids 2/9, 6/13, 13/17, 17/20, 20/27, 20/24, 35/39, 39/46,
      and 39/43 shown in SEQ ID NO: 1 can be cross-linked or wherein
      amino acids 8 and 12 are modified amino acids that form an
      internal cross-link.

<400> SEQUENCE: 8

Glu Arg Leu Arg Arg Arg Ile Glu Leu Cys Arg Arg His His Ser Thr
1               5                   10                  15

<210> SEQ ID NO 9
<211> LENGTH: 17
<212> TYPE: PRT
<213> ORGANISM: Homo sapiens
<220> FEATURE:
<223> OTHER INFORMATION: Amino acids 8 and 12 are modified amino acids
      that form an internal cross-link.

<400> SEQUENCE: 9

Glu Arg Leu Arg Ala Arg Ile Ala Val Cys Arg Gln His His Leu Ser
1               5                   10                  15

Cys

<210> SEQ ID NO 10
<211> LENGTH: 16
<212> TYPE: PRT
<213> ORGANISM: Homo sapiens
<220> FEATURE:
<223> OTHER INFORMATION: Amino acids 8 and 12 are modified amino acids
      that form an internal cross-link.

<400> SEQUENCE: 10

Glu Arg Leu Arg Gln Arg Ile Glu Gly Cys Arg Arg His His Val Asn
1               5                   10                  15

<210> SEQ ID NO 11
<211> LENGTH: 55
<212> TYPE: PRT
<213> ORGANISM: Homo sapiens
<220> FEATURE:
<223> OTHER INFORMATION: Wherein at least one pair of amino acids are
      modified amino acids that form an internal cross-link.

<400> SEQUENCE: 11

His Ser Ala Val Met Glu Arg Leu Arg Arg Arg Ile Glu Leu Cys Arg
1               5                   10                  15

Arg His His Ser Thr Cys Glu Ala Arg Tyr Glu Ala Val Ser Pro Glu
            20                  25                  30

Arg Leu Glu Leu Glu Arg Gln His Thr Phe Ala Leu His Gln Arg Cys
        35                  40                  45

Ile Gln Ala Lys Ala Lys Arg
    50                  55

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12
```

```
Ala Val Met Glu Arg Leu
1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Arg Leu Arg Arg Arg Ile
1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Leu Cys Arg Arg His His
1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Thr Cys Glu Ala Arg Tyr
1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Cys Glu Ala Arg Tyr Glu
1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Leu Glu Arg Gln His Thr
1               5

<210> SEQ ID NO 18
<211> LENGTH: 6
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 18

His Thr Phe Ala Leu His
1               5

<210> SEQ ID NO 19
<211> LENGTH: 62
<212> TYPE: PRT
<213> ORGANISM: Homo sapiens

<400> SEQUENCE: 19

Leu Pro Arg His Ser Ala Val Met Glu Arg Leu Arg Arg Ile Glu
1               5                   10                  15

Leu Cys Arg Arg His His Ser Thr Cys Glu Ala Arg Tyr Glu Ala Val
                20                  25                  30

Ser Pro Glu Arg Leu Glu Leu Glu Arg Gln His Thr Phe Ala Leu His
            35                  40                  45

Gln Arg Cys Ile Gln Ala Lys Ala Lys Arg Ala Gly Lys His
        50                  55                  60

<210> SEQ ID NO 20
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Leu Pro Arg His Ser Ala Val Met Glu Arg Leu Arg Arg Ile Glu
1               5                   10                  15

Leu Cys Arg Arg His His Ser Thr Cys Glu Ala Arg Tyr Glu Ala Val
                20                  25                  30

Ser Pro Glu Arg Leu Glu Leu Glu Arg Gln His Thr Phe Ala Leu His
            35                  40                  45

Gln Arg Cys Ile Gln Ala Lys Ala Lys Arg Ala Gly Lys His
        50                  55                  60

<210> SEQ ID NO 21
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: Any modified amino acid forming a cross-link
<220> FEATURE:
<221> NAME/KEY: MOD_RES
<222> LOCATION: (20)..(20)
<223> OTHER INFORMATION: Any modified amino acid forming a cross-link

<400> SEQUENCE: 21

Leu Pro Arg His Ser Ala Val Met Glu Arg Leu Arg Arg Ile Xaa
1               5                   10                  15

Leu Cys Arg Xaa His His Ser Thr Cys Glu Ala Arg Tyr Glu Ala Val
                20                  25                  30

Ser Pro Glu Arg Leu Glu Leu Glu Arg Gln His Thr Phe Ala Leu His
            35                  40                  45
```

Gln Arg Cys Ile Gln Ala Lys Ala Lys Arg Ala Gly Lys His
        50                  55                  60

<210> SEQ ID NO 22
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: Any modified amino acid forming a cross-link
<220> FEATURE:
<221> NAME/KEY: MOD_RES
<222> LOCATION: (20)..(20)
<223> OTHER INFORMATION: Any modified amino acid forming a cross-link

<400> SEQUENCE: 22

Leu Pro Arg His Ser Ala Val Met Glu Arg Leu Arg Arg Arg Ile Xaa
1               5                   10                  15

Leu Ser Arg Xaa His His Ser Thr Cys Glu Ala Arg Tyr Glu Ala Val
            20                  25                  30

Ser Pro Glu Arg Leu Glu Leu Glu Arg Gln His Thr Phe Ala Leu His
        35                  40                  45

Gln Arg Cys Ile Gln Ala Lys Ala Lys Arg Ala Gly Lys His
        50                  55                  60

<210> SEQ ID NO 23
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: Any modified amino acid forming a cross-link
<220> FEATURE:
<221> NAME/KEY: MOD_RES
<222> LOCATION: (20)..(20)
<223> OTHER INFORMATION: Any modified amino acid forming a cross-link

<400> SEQUENCE: 23

Leu Pro Arg His Ser Ala Val Met Glu Arg Leu Arg Arg Arg Ile Xaa
1               5                   10                  15

Leu Ala Arg Xaa His His Ser Thr Cys Glu Ala Arg Tyr Glu Ala Val
            20                  25                  30

Ser Pro Glu Arg Leu Glu Leu Glu Arg Gln His Thr Phe Ala Leu His
        35                  40                  45

Gln Arg Cys Ile Gln Ala Lys Ala Lys Arg Ala Gly Lys His
        50                  55                  60

<210> SEQ ID NO 24
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: Any modified amino acid forming a cross-link
<220> FEATURE:

```
<221> NAME/KEY: MOD_RES
<222> LOCATION: (23)..(23)
<223> OTHER INFORMATION: Any modified amino acid forming a cross-link

<400> SEQUENCE: 24

Leu Pro Arg His Ser Ala Val Met Glu Arg Leu Arg Arg Arg Ile Xaa
1               5                   10                  15

Leu Ser Arg Arg His His Xaa Thr Cys Glu Ala Arg Tyr Glu Ala Val
            20                  25                  30

Ser Pro Glu Arg Leu Glu Leu Glu Arg Gln His Thr Phe Ala Leu His
        35                  40                  45

Gln Arg Cys Ile Gln Ala Lys Ala Lys Arg Ala Gly Lys His
    50                  55                  60

<210> SEQ ID NO 25
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: Any modified amino acid forming a cross-link
<220> FEATURE:
<221> NAME/KEY: MOD_RES
<222> LOCATION: (23)..(23)
<223> OTHER INFORMATION: Any modified amino acid forming a cross-link

<400> SEQUENCE: 25

Leu Pro Arg His Ser Ala Val Met Glu Arg Leu Arg Arg Arg Ile Xaa
1               5                   10                  15

Leu Ala Arg Arg His His Xaa Thr Cys Glu Ala Arg Tyr Glu Ala Val
            20                  25                  30

Ser Pro Glu Arg Leu Glu Leu Glu Arg Gln His Thr Phe Ala Leu His
        35                  40                  45

Gln Arg Cys Ile Gln Ala Lys Ala Lys Arg Ala Gly Lys His
    50                  55                  60

<210> SEQ ID NO 26
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (42)..(42)
<223> OTHER INFORMATION: Any modified amino acid forming a cross-link
<220> FEATURE:
<221> NAME/KEY: MOD_RES
<222> LOCATION: (46)..(46)
<223> OTHER INFORMATION: Any modified amino acid forming a cross-link

<400> SEQUENCE: 26

Leu Pro Arg His Ser Ala Val Met Glu Arg Leu Arg Arg Arg Ile Glu
1               5                   10                  15

Leu Cys Arg Arg His His Ser Thr Cys Glu Ala Arg Tyr Glu Ala Val
            20                  25                  30

Ser Pro Glu Arg Leu Glu Leu Glu Arg Xaa His Thr Phe Xaa Leu His
        35                  40                  45

Gln Arg Cys Ile Gln Ala Lys Ala Lys Arg Ala Gly Lys His
    50                  55                  60
```

```
<210> SEQ ID NO 27
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (42)..(42)
<223> OTHER INFORMATION: Any modified amino acid forming a cross-link
<220> FEATURE:
<221> NAME/KEY: MOD_RES
<222> LOCATION: (49)..(49)
<223> OTHER INFORMATION: Any modified amino acid forming a cross-link

<400> SEQUENCE: 27

Leu Pro Arg His Ser Ala Val Met Glu Arg Leu Arg Arg Arg Ile Glu
1               5                   10                  15

Leu Cys Arg Arg His His Ser Thr Cys Glu Ala Arg Tyr Glu Ala Val
                20                  25                  30

Ser Pro Glu Arg Leu Glu Leu Glu Arg Xaa His Thr Phe Ala Leu His
        35                  40                  45

Xaa Arg Cys Ile Gln Ala Lys Ala Lys Arg Ala Gly Lys His
    50                  55                  60

<210> SEQ ID NO 28
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (42)..(42)
<223> OTHER INFORMATION: Any modified amino acid forming a cross-link
<220> FEATURE:
<221> NAME/KEY: MOD_RES
<222> LOCATION: (49)..(49)
<223> OTHER INFORMATION: Any modified amino acid forming a cross-link

<400> SEQUENCE: 28

Leu Pro Arg His Ser Ala Val Met Glu Arg Leu Arg Arg Arg Ile Glu
1               5                   10                  15

Leu Cys Arg Arg His His Ser Thr Cys Glu Ala Arg Tyr Glu Ala Val
                20                  25                  30

Ser Pro Glu Arg Leu Glu Leu Glu Arg Xaa His Thr Ala Ala Leu His
        35                  40                  45

Xaa Arg Cys Ile Gln Ala Lys Ala Lys Arg Ala Gly Lys His
    50                  55                  60

<210> SEQ ID NO 29
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: Any modified amino acid forming a cross-link
<220> FEATURE:
<221> NAME/KEY: MOD_RES
<222> LOCATION: (23)..(23)
<223> OTHER INFORMATION: Any modified amino acid forming a cross-link
```

<400> SEQUENCE: 29

Leu Pro Arg His Ser Ala Val Met Glu Arg Leu Arg Arg Arg Ile Xaa
1               5                   10                  15

Leu Ala Arg Arg His His Xaa Thr Ala Glu Ala Arg Tyr Glu Ala Val
            20                  25                  30

Ser Pro Glu Arg Leu Glu Leu Glu Arg Gln His Thr Phe Ala Leu His
        35                  40                  45

Gln Arg Cys Ile Gln Ala Lys Ala Lys Arg Ala Gly Lys His
    50                  55                  60

<210> SEQ ID NO 30
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (12)..(12)
<223> OTHER INFORMATION: Any modified amino acid forming a cross-link
<220> FEATURE:
<221> NAME/KEY: MOD_RES
<222> LOCATION: (16)..(16)
<223> OTHER INFORMATION: Any modified amino acid forming a cross-link
<220> FEATURE:
<221> NAME/KEY: MOD_RES
<222> LOCATION: (23)..(23)
<223> OTHER INFORMATION: Any modified amino acid forming a cross-link
<220> FEATURE:
<221> NAME/KEY: MOD_RES
<222> LOCATION: (27)..(27)
<223> OTHER INFORMATION: Any modified amino acid forming a cross-link

<400> SEQUENCE: 30

Leu Pro Arg His Ser Ala Val Met Glu Arg Leu Xaa Arg Arg Ile Xaa
1               5                   10                  15

Leu Ala Arg Arg His His Xaa Thr Ala Glu Xaa Arg Tyr Glu Ala Val
            20                  25                  30

Ser Pro Glu Arg Leu Glu Leu Glu Arg Gln His Thr Phe Ala Leu His
        35                  40                  45

Gln Arg Cys Ile Gln Ala Lys Ala Lys Arg Ala Gly Lys His
    50                  55                  60

<210> SEQ ID NO 31
<211> LENGTH: 62
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (23)..(23)
<223> OTHER INFORMATION: Any modified amino acid forming a cross-link
<220> FEATURE:
<221> NAME/KEY: MOD_RES
<222> LOCATION: (27)..(27)
<223> OTHER INFORMATION: Any modified amino acid forming a cross-link

<400> SEQUENCE: 31

Leu Pro Arg His Ser Ala Val Met Glu Arg Leu Arg Arg Arg Ile Glu
1               5                   10                  15

Leu Cys Arg Arg His His Xaa Thr Cys Glu Xaa Arg Tyr Glu Ala Val
            20                  25                  30

Ser Pro Glu Arg Leu Glu Leu Glu Arg Gln His Thr Phe Ala Leu His
            35                  40                  45

Gln Arg Cys Ile Gln Ala Lys Ala Lys Arg Ala Gly Lys His
     50                  55                  60

<210> SEQ ID NO 32
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

His Ser Ala Val Met Glu Leu Arg Ile Glu Arg Ser Thr Ala Glu Ala
1               5                   10                  15

Arg Leu Glu Leu Arg Gln Phe Ala Gln Arg Ile Gln Ala Ala Lys Arg
            20                  25                  30

<210> SEQ ID NO 33
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any modified amino acid forming a cross-link
<220> FEATURE:
<221> NAME/KEY: MOD_RES
<222> LOCATION: (12)..(12)
<223> OTHER INFORMATION: Any modified amino acid forming a cross-link

<400> SEQUENCE: 33

Glu Arg Leu Arg Arg Arg Ile Xaa Leu Cys Arg Xaa His His Ser Thr
1               5                   10                  15

<210> SEQ ID NO 34
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any modified amino acid forming a cross-link
<220> FEATURE:
<221> NAME/KEY: MOD_RES
<222> LOCATION: (12)..(12)
<223> OTHER INFORMATION: Any modified amino acid forming a cross-link

<400> SEQUENCE: 34

Glu Arg Leu Arg Arg Arg Ile Xaa Leu Ser Arg Xaa His His Ser Thr
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any modified amino acid forming a cross-link

```
<220> FEATURE:
<221> NAME/KEY: MOD_RES
<222> LOCATION: (12)..(12)
<223> OTHER INFORMATION: Any modified amino acid forming a cross-link

<400> SEQUENCE: 35

Glu Arg Leu Arg Arg Arg Ile Xaa Leu Ala Arg Xaa His His Ser Thr
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any modified amino acid forming a cross-link
<220> FEATURE:
<221> NAME/KEY: MOD_RES
<222> LOCATION: (15)..(15)
<223> OTHER INFORMATION: Any modified amino acid forming a cross-link

<400> SEQUENCE: 36

Glu Arg Leu Arg Arg Arg Ile Xaa Leu Ser Arg Arg His His Xaa Thr
1               5                   10                  15

<210> SEQ ID NO 37
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any modified amino acid forming a cross-link
<220> FEATURE:
<221> NAME/KEY: MOD_RES
<222> LOCATION: (15)..(15)
<223> OTHER INFORMATION: Any modified amino acid forming a cross-link

<400> SEQUENCE: 37

Glu Arg Leu Arg Arg Arg Ile Xaa Leu Ala Arg Arg His His Xaa Thr
1               5                   10                  15

<210> SEQ ID NO 38
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any modified amino acid forming a cross-link
<220> FEATURE:
<221> NAME/KEY: MOD_RES
<222> LOCATION: (10)..(10)
<223> OTHER INFORMATION: Any modified amino acid forming a cross-link

<400> SEQUENCE: 38

Leu Glu Leu Glu Arg Xaa His Thr Phe Xaa Leu His Gln Arg
1               5                   10

<210> SEQ ID NO 39
<211> LENGTH: 14
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any modified amino acid forming a cross-link
<220> FEATURE:
<221> NAME/KEY: MOD_RES
<222> LOCATION: (13)..(13)
<223> OTHER INFORMATION: Any modified amino acid forming a cross-link

<400> SEQUENCE: 39

Leu Glu Leu Glu Arg Xaa His Thr Phe Ala Leu His Xaa Arg
1               5                   10

<210> SEQ ID NO 40
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Any modified amino acid forming a cross-link
<220> FEATURE:
<221> NAME/KEY: MOD_RES
<222> LOCATION: (13)..(13)
<223> OTHER INFORMATION: Any modified amino acid forming a cross-link

<400> SEQUENCE: 40

Leu Glu Leu Glu Arg Xaa His Thr Ala Ala Leu His Xaa Arg
1               5                   10

<210> SEQ ID NO 41
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any modified amino acid forming a cross-link
<220> FEATURE:
<221> NAME/KEY: MOD_RES
<222> LOCATION: (15)..(15)
<223> OTHER INFORMATION: Any modified amino acid forming a cross-link

<400> SEQUENCE: 41

Glu Arg Leu Arg Arg Arg Ile Xaa Leu Ala Arg Arg His His Xaa Thr
1               5                   10                  15

Ala Glu Ala Arg Tyr
            20

<210> SEQ ID NO 42
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Any modified amino acid forming a cross-link
<220> FEATURE:
```

```
<221> NAME/KEY: MOD_RES
<222> LOCATION: (8)..(8)
<223> OTHER INFORMATION: Any modified amino acid forming a cross-link
<220> FEATURE:
<221> NAME/KEY: MOD_RES
<222> LOCATION: (15)..(15)
<223> OTHER INFORMATION: Any modified amino acid forming a cross-link
<220> FEATURE:
<221> NAME/KEY: MOD_RES
<222> LOCATION: (19)..(19)
<223> OTHER INFORMATION: Any modified amino acid forming a cross-link

<400> SEQUENCE: 42

Glu Arg Leu Xaa Arg Arg Ile Xaa Leu Ala Arg Arg His His Xaa Thr
1               5                   10                  15

Ala Glu Xaa Arg Tyr
            20

<210> SEQ ID NO 43
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any modified amino acid forming a cross-link
<220> FEATURE:
<221> NAME/KEY: MOD_RES
<222> LOCATION: (12)..(12)
<223> OTHER INFORMATION: Any modified amino acid forming a cross-link

<400> SEQUENCE: 43

Glu Leu Cys Arg Arg His His Xaa Thr Cys Glu Xaa Arg Tyr Glu Ala
1               5                   10                  15

Val

<210> SEQ ID NO 44
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)..(8)
<223> OTHER INFORMATION: Any modified amino acid forming a cross-link
<220> FEATURE:
<221> NAME/KEY: MOD_RES
<222> LOCATION: (12)..(12)
<223> OTHER INFORMATION: Any modified amino acid forming a cross-link

<400> SEQUENCE: 44

Glu Arg Leu Glu Leu Glu Arg Xaa His Thr Phe Xaa Leu His Gln Arg
1               5                   10                  15
```

STABILIZED MAML PEPTIDES AND USES THEREOF

This application is a continuation of PCT/US2007/084838, filed Nov. 15, 2007, which claims priority to U.S. Application No. 60/859,379, filed Nov. 15, 2006, the entire contents of which are incorporated herein.

BACKGROUND

Notch receptors are transmembrane receptors that involved in a variety of important signaling pathways. Mutations in human NOTCH1 are commonly found in human T cell acute lymphoblastic leukemias (T-ALL) and it is thought that abnormalities in Notch signaling are involved in other cancers.

The Notch signaling pathway is complex. When an appropriate ligand binds to Notch a proteolytic event occurs which allows a portion of the Notch receptor called ICN to enter the cell nucleus where is interacts with CSL, a transcription factor that binds DNA, and a protein that is a member of the Mastermind-like (MAML) family. The assembled complex can active transcription of certain genes. It is known that certain fragments of MAML (e.g., within amino acids 13-74 of human MAML-1) can act to interfere with Notch activation of transcription.

SUMMARY

Described below are stably cross-linked a polypeptides related to human MAML. These cross-linked polypeptides contain at least two modified amino acids that together form an internal cross-link (also referred to as a tether) that can help to stabilize the alpha-helical secondary structure that is thought to be important for binding of MAML peptides to the Notch transcription complex, a complex that includes ICN and CSL. It is thought that the constrained secondary structure can increase resistance of the polypeptide to proteolytic cleavage. Accordingly, a cross-linked polypeptide described herein can have improved biological activity relative to a corresponding polypeptide that is not cross-linked. The cross-linked polypeptides described herein can be used therapeutically, e.g., to treat a variety of cancers in a subject. Inhibitors of Notch function may be useful in reducing unwanted immune responses, undesirable angiogenesis, treatment of human T cell acute lymphoblastic leukemias, treatment of mucoepidermoid carcinomas, treatment of breast cancer, treatment of medulloblastoma, and treatment of pancreatic cancer, treatment of lung cancer, treatment of ovarian cancer, treatment of atherosclerosis (e.g., heart disease), treatment of melanoma, treatment of colon cancer, and treatment of cancers that exhibit resistance to gamma secretase inhibitors.

In one aspect, the invention features a modified polypeptide of Formula (I),

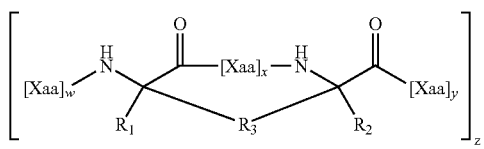

Formula (I)

wherein;

each $R_1$ and $R_2$ are independently H or a $C_1$ to $C_{10}$ alkyl, alkenyl, alkynyl, arylalkyl, cycloalkylalkyl, heteroarylalkyl, or heterocyclylalkyl;

$R_3$ is alkyl, alkenyl, alkynyl; $[R_4—K—R_4]_n$; each of which is substituted with 0-6 $R_5$;

$R_4$ is alkyl, alkenyl, or alkynyl;

$R_5$ is halo, alkyl, $OR_6$, $N(R_6)_2$, $SR_6$, $SOR_6$, $SO_2R_6$, $CO_2R_6$, $R_6$, a fluorescent moiety, or a radioisotope;

K is O, S, SO, $SO_2$, CO, $CO_2$, $CONR_6$, or

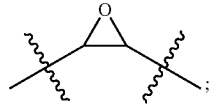

$R_6$ is H, alkyl, or a therapeutic agent;

n is 3, 4 or 6;

x is an integer from 2-10;

w and y are independently an integer from 0-100 (e.g., 1, 2, 3, 4, 5, 6 or 7);

z is an integer from 1-10 (e.g., 1, 2, 3, 4, 5, 6, 7, 8, 9, 10); and each Xaa is independently an amino acid, wherein the polypeptide comprises at least 8 (e.g., 8, 9, 10, 11, 12, 13 or more) contiguous amino acids of SEQ ID NO:1, 2, 3, 4, 5, 6 or 7 except that: (a) within the 8 contiguous amino acids of SEQ ID NO:1, 2, 3, 4, 5, 6 or 7 the side chains of at least one pair of amino acids separated by 3, 4 or 6 amino acids is replaced by the linking group $R_3$ which connects the alpha carbons of the pair of amino acids as depicted in formula I; and (b) the alpha carbon of the first of the pair of amino acids is substituted with $R_1$ as depicted in formula I and the alpha carbon of the second of the pair of amino acids is substituted with $R_2$ as depicted in formula I or a pharmaceutically acceptable salt thereof.

SEQ ID NO:1 is a sequence created from an alignment of human MAML-1, 2, and 3, starting at amino acid 19 of MAML-1 and extending to amino acid 61. SEQ ID NOs:2-4 respectively are the amino acid sequences of MAML-1, 2 and 3 over this same region. SEQ ID NOs:5-7 respectively are the amino acid sequences of MAML-1, 2 and 3 over a somewhat larger region.

His$_1$ Ser$_2$ Xaa$_3$ Xaa$_4$ Xaa$_5$ Glu$_6$ Arg$_7$ Leu$_8$ Arg$_9$ Xaa$_{10}$ Xaa$_{11}$ Ile$_{12}$ Xaa$_{13}$ Xaa$_{14}$ Cys$_{15}$ Arg$_{16}$ Xaa$_{17}$ His$_{18}$ His$_{19}$ Xaa$_{20}$ Xaa$_{21}$ Cys$_{22}$ Glu$_{23}$ Xaa$_{24}$ Arg$_{25}$ Tyr$_{26}$ Xaa$_{27}$ Xaa$_{28}$ Xaa$_{29}$ Xaa$_{30}$ Xaa$_{31}$ Glu$_{32}$ Xaa$_{33}$ Xaa$_{34}$ Xaa$_{35}$ Xaa$_{36}$ Glu$_{37}$ Arg$_{38}$ Xaa$_{39}$ Xaa$_{40}$ Thr$_{41}$ Xaa$_{42}$ Xaa$_{43}$ Leu$_{44}$ Xaa$_{45}$ Xaa$_{46}$ Xaa$_{47}$ (SEQ ID NO:1), wherein Xaa$_3$ is Ala or Thr;
Xaa$_4$ is Val or Ile;
Xaa$_5$ is Met or Val;
Xaa$_{10}$ is Arg, Ala, or Gln
Xaa$_{13}$ is Glu or Ala
Xaa$_{14}$ is Leu, Val or Gly
Xaa$_{17}$ Arg or Gln
Xaa$_{20}$ is Ser, Leu or Val
Xaa$_{21}$ is Thr, Ser or Asn
Xaa$_{24}$ is Arg, Gly or Asn
Xaa$_{27}$ is Glu or Gln
Xaa$_{28}$ is Ala, Arg or Gln
Xaa$_{29}$ is Val, Gly or Ala
Xaa$_{30}$ is Ser, Arg or Gln
Xaa$_{31}$ Pro, Ala or Val
Xaa$_{33}$ Arg, Ser or Gln
Xaa$_{34}$ Leu or Ser
Xaa$_{35}$ is Glu or Asp Xaa₃₆ is Leu or Arg
Xaa₃₉ is Gln Glu or Arg
Xaa₄₀ is His, Ser or Asp
Xaa₄₂ is Phe, Leu or Val
Xaa₄₃ is Ala, Gln or Ser
Xaa₄₅ is His, Leu or Tyr
Xaa₄₆ is Gln or Ser
Xaa₄₇ is Arg or Leu Within SEQ ID NO:1, the following pairs of amino acid can be cross-linked: 2/9, 6/13, 13/17, 17/20, 20/27, 20/24, 35/39, 39/46, and 39/43. The corresponding residues in SEQ ID NOs:2-8 and 11 can be cross-linked.

```
SEQ ID NO: 2 (MAML-1; amino acids 19-62):
VMERLRRRIELCRRHHSTCEARYEAVSPERLELERQHTFALHQR

SEQ ID NO: 3 (MAML-2):
IVERLRARIAVCRQHHLSCEGRYERGRAESSDRERESTLQLLSL

SEQ ID NO: 4 (MAML-3):
VVERLRQRIEGCRRHHVNCENRYQQAQVEQLELERRDTVSLYQR

SEQ ID NO: 5 (MAML-1; includes predicted domain for
binding the transcription complex):
HSAVMERLRRRIELCRRHHSTCEARYEAVSPERLELERQHTFALHQRCIQ
AKAKRAGKH SEQ ID NO: 6 (MAML-2; includes predicted domain for
binding the transcription complex):
HSAIVERLRARIAVCRQHHLSCEGRYERGRAESSDRERESTLQLLSLVQH
GQGARKAGKH SEQ ID NO: 7 (MAML-3; includes predicted domain for
binding the transcription complex):
AVPKHSTVVERLRQRIEGCRRHHVNCENRYQQAQVEQLELERRDTVSLYQ
RTLEQRAKKS SEQ ID NO: 8 (MAML-1 core)
ERLRRRIELCRRHHST SEQ ID NO: 9 (MAML-2 core)
ERLRARIAVCRQHHLSC SEQ ID NO: 10 (MAML-3 core)
ERLRQRIEGCRRHHVN
```

In some instances, the modified polypeptide binds a complex of ICN and CSL, e.g., ICN and CSL bound to DNA.

In some instances, each y is independently an integer between 3 and 15.

In some instances each y is independently an integer between 1 and 15.

In some instances, $R_1$ and $R_2$ are each independently H or $C_1$-$C_6$ alkyl.

In some instances, $R_1$ and $R_2$ are each independently $C_1$-$C_3$ alkyl.

In some instances, at least one of $R_1$ and $R_2$ are methyl. For example $R_1$ and $R_2$ are both methyl.

In some instances $R_3$ is alkyl (e.g., $C_8$ alkyl) and x is 3.
In some instances, $R_3$ is $C_{11}$ alkyl and x is 6.
In some instances, $R_3$ is alkenyl (e.g., $C_8$ alkenyl) and x is 3.
In some instances x is 6 and $R_3$ is $C_{11}$ alkenyl.
In some instances, $R_3$ is a straight chain alkyl, alkenyl, or alkynyl.
In some instances $R_3$ is —CH₂CH₂—CH₂—CH=CH—CH₂—CH₂—CH₂—.

In certain embodiments the two alpha, alpha disubstituted stereocenters (alpha carbons) are both in the R configuration or S configuration (e.g., i, i+4 cross-link), or one stereocenter is R and the other is S (e.g., i, i+7 cross-link). Thus, where Formula I is depicted as

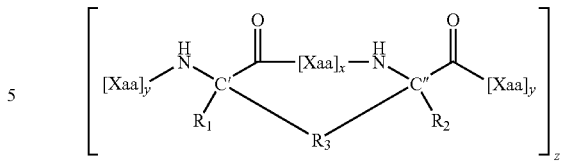

the C' and C" disubstituted stereocenters can both be in the R configuration or they can both be in the S configuration, for example when x is 3. When x is 6, the C' disubstituted stereocenter is in the R configuration and the C" disubstituted stereocenter is in the S configuration.

The $R_3$ double bond may be in the E or Z stereochemical configuration.

In some instances $R_3$ is [$R_4$—K—$R_4$]; and $R_4$ is a straight chain alkyl, alkenyl, or alkynyl.

In some instances, the polypeptide includes an amino acid sequence which is at least about 60% (70%, 80%, 85%, 90%, 95% or 98%) identical to the amino acid sequence of HSAVMERLRRRIELCRRHHSTCEARYEAVSPERLELERQHTFALHQRCIQAKAKR (SEQ ID NO: 8). In some instances the modified polypeptide comprises at least 8 contiguous amino acids of HSAVMERLRRRIELCRRHHSTCEARYEAVSPERLELERQHTFALHQRCIQAKAKR (SEQ ID NO: 8). except that at least one pair of amino acids within the 8 (e.g., 8, 9, 10, 11, 12, 13 or more) contiguous amino acids are replaced by modified amino acids that can form an internal cross-link.

The tether can include an alkyl, alkenyl, or alkynyl moiety (e.g., $C_5$, $C_8$ or $C_{11}$ alkyl or a $C_5$, $C_8$ or $C_{11}$ alkenyl, or $C_5$, $C_8$ or $C_{11}$ alkynyl). The tethered amino acid can be alpha disubstituted (e.g., $C_1$-$C_3$ or methyl). [Xaa]$_y$ and [Xaa]$_w$ are peptides that can independently comprise at least 1, 2 3, 4, 5, 6, 7, 8, 9, 10, 11, 12, 13, 14, 15, 16, 17, 18, 19, 20, 25 or more contiguous amino acids of a MAML polypeptide and [Xaa]$_x$ is a peptide that can comprise 3 or 6 contiguous amino acids of acids of a MAML peptide.

The polypeptide can comprise 8, 9, 10, 11, 12, 13, 14, 15, 16, 17, 18, 19, 20, 25, 30, 35, 40, 45, 50 amino acids of a MAML polypeptide (e.g., human MAML-1, 2 or 3 or a consensus MAML polypeptide). The amino acids are contiguous except that one or more pairs of amino acids separated by 3 or 6 amino acids are replaced by amino acid substitutes that form a cross-link, e.g., via $R_3$. Thus, at least two amino acids can be replaced by tethered amino acids or tethered amino acid substitutes. Thus, where formula I is depicted as

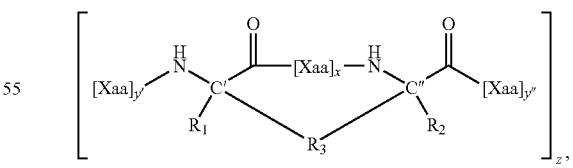

[Xaa]$_{y'}$ and [Xaa]$_{y''}$ can each comprise contiguous polypeptide sequences from the same or different MAML peptides.

In some instances the polypeptide comprises an amino acid sequence selected from SEQ ID NOs:8, 9, 10, and 11, wherein: (a) the side chains of amino acids 8 and 12 are replaced by the linking group $R_3$ which connects the alpha carbons of amino acids 8 and 12 as depicted in formula I; and (b) the alpha carbon of amino acid 8 is substituted with $R_1$ as depicted in formula I and the alpha carbon of amino acid 12 is substituted with $R_2$ as depicted in formula I.

The invention features cross-linked polypeptides comprising at least 8 (e.g., 8, 9, 10, 11, 12, 13, 14, 15, 16, 17, 18, 19, 20, 21, 22, 23, 24, 25, 30, 35, 40, 45, 50 or more) contiguous amino acids of a MAML polypeptide wherein the alpha carbons of two amino acids that are separated by three amino acids (or six amino acids) are linked via $R_3$, one of the two alpha carbons is substituted by $R_1$ and the other is substituted by $R_2$ and each is linked via peptide bonds to additional amino acids.

In some embodiments the polypeptide acts as dominant negative inhibitor of Notch.

In some instances, the polypeptide also includes a fluorescent moiety or radioisotope.

In some instances, $R_1$ and $R_2$ are methyl; $R_3$ is $C_8$ alkyl, $C_{11}$ alkyl, $C_8$ alkenyl, $C_{11}$ alkenyl, $C_8$ alkynyl, or $C_{11}$ alkynyl; and x is 2, 3, or 6.

In some instances, the polypeptide includes an PEG, tat protein, affinity label, a targeting moiety, and/or a biotin moiety.

In another aspect, the invention features a method of making a polypeptide of Formula (III), including
providing a polypeptide of Formula (II); and Formula (II)

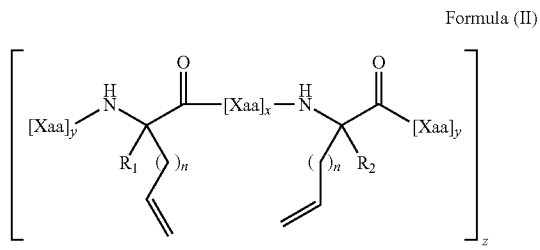

treating the compound of Formula (II) with a catalyst to promote a ring closing metathesis, thereby providing a compound of formula (III)

Formula (III)

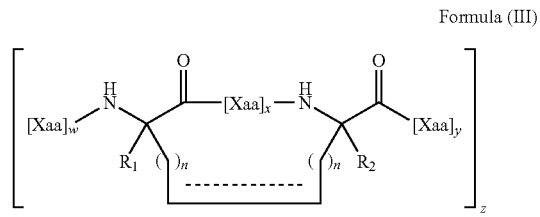

wherein
each $R_1$ and $R_2$ are independently H, alkyl, alkenyl, alkynyl, arylalkyl, cycloalkylalkyl; heteroarylalkyl; or heterocyclylalkyl;
each n is independently an integer from 1-15;
x is 2, 3, or 6
w and y are independently an integer from 0-100;
z is an integer from 1-10 (e.g., 1, 2, 3, 4, 5, 6, 7, 8, 9, 10); and
each Xaa is independently an amino acid;
In some instances, the polypeptide binds to a complex of ICN and CSL.
In some instances, the catalyst is a ruthenium catalyst.
In some instances, the method also includes providing a reducing or oxidizing agent subsequent to the ring closing metathesis.

In some instances, the reducing agent is $H_2$ or the oxidizing agent is osmium tetroxide In some instances, the invention features a method of treating a subject including administering to the subject any of the compounds described herein. In some instances, the method also includes administering an additional therapeutic agent.

In some instances, the invention features a method of treating cancer in a subject including administering to the subject any of the compounds described herein. In some instances, the method also includes administering an additional therapeutic agent.

In some instances, the invention features a library of the compounds described herein.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., therapeutic administration to a subject or generation of reagents to study or discover a biological pathway either in vitro or in vivo).

The compounds of this invention may contain one or more asymmetric centers and thus occur as racemates and racemic mixtures, single enantiomers, individual diastereomers and diastereomeric mixtures. All such isomeric forms of these compounds are expressly included in the present invention. The compounds of this invention may also be represented in multiple tautomeric forms, in such instances, the invention expressly includes all tautomeric forms of the compounds described herein (e.g., alkylation of a ring system may result in alkylation at multiple sites, the invention expressly includes all such reaction products). All such isomeric forms of such compounds are expressly included in the present invention. All crystal forms of the compounds described herein are expressly included in the present invention.

The term "amino acid" refers to a molecule containing both an amino group and a carboxyl group. Suitable amino acids include, without limitation, both the D- and L-isomers of the 20 common naturally occurring amino acids found in peptides (e.g., A, R, N, C, D, Q, E, G, H, I, L, K, M, F, P, S, T, W, Y, V (as known by the one letter abbreviations)) as well as the naturally occurring and unnaturally occurring amino acids prepared by organic synthesis or other metabolic routes. The table below provides the structures of the side chains for each of the 20 common naturally-occurring amino acids. In this table the "—" at right side of each structure is the bond to the alpha carbon.

| Amino acid | Single Letter | Three Letter | Structure of side chain |
|---|---|---|---|
| Alanine | A | Ala | $CH_3$— |
| Arginine | R | Arg | $HN{=}C(NH_2){-}NH{-}(CH_2)_3{-}$ |
| Asparagine | N | Asn | $H_2N{-}C(O){-}CH_2{-}$ |
| Aspartic acid | D | Asp | $HO(O)C{-}CH_2{-}$ |
| Cysteine | C | Cys | $HS{-}CH_2{-}$ |
| Glutamine | Q | Gln | $H_2N{-}C(O){-}(CH_2)_2{-}$ |
| Glutamic acid | E | Glu | $HO(O)C{-}(CH_2)_2{-}$ |
| Glycine | G | Gly | H— |
| Histidine | H | His | $N{=}CH{-}NH{-}CH{=}C{-}CH_2{-}$ |
| Isoleucine | I | Ile | $CH_3{-}CH_2{-}CH(CH_3){-}$ |
| Leucine | L | Leu | $(CH_3)_2{-}CH{-}CH_2{-}$ |
| Lysine | K | Lys | $H_2N{-}(CH_2)_4{-}$ |

-continued

| Amino acid | Single Letter | Three Letter | Structure of side chain |
|---|---|---|---|
| Methionine | M | Met | $CH_3-S-(CH_2)_2-$ |
| Phenyl-alanine | F | Phe | Phenyl-$CH_2-$ |
| Proline | P | Pro | —N—$(CH_2)_3$—CH— |
| Serine | F | Ser | HO—$CH_2-$ |
| Threonine | T | Thr | $CH_3-CH(OH)-$ |
| Tryptophan | W | Trp | Phenyl-NH—CH=C—$CH_2-$ |
| Tyrosine | Y | Tyr | 4-OH-Phenyl-$CH_2-$ |
| Valine | V | Val | $CH_3-CH(CH_2)-$ |

A "non-essential" amino acid residue is a residue that can be altered from the wild-type sequence of a polypeptide (without abolishing or substantially altering its activity. An "essential" amino acid residue is a residue that, when altered from the wild-type sequence of the polypeptide, results in abolishing or substantially abolishing the polypeptide activity.

A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a MAML polypeptide, for example, is preferably replaced with another amino acid residue from the same side chain family.

The symbol "⌇" when used as part of a molecular structure refers to a single band or a trans or cis double bond.

The term "amino acid side chain" refers to a moiety attached to the α-carbon in an amino acids. For example, the amino acid side chain for alanine is methyl, the amino acid side chain for phenylalanine is phenylmethyl, the amino acid side chain for cysteine is thiomethyl, the amino acid side chain for aspartate is carboxymethyl, the amino acid side chain for tyrosine is 4-hydroxyphenylmethyl, etc. Other non-naturally occurring amino acid side chains are also included, for example, those that occur in nature (e.g., an amino acid metabolite) or those that are made synthetically (e.g., an alpha di-substituted amino acid).

The term polypeptide encompasses two or more naturally occurring or synthetic amino acids linked by a covalent bond (e.g., a amide bond). Polypeptides as described herein include full length proteins (e.g., fully processed proteins) as well as shorter amino acids sequences (e.g., fragments of naturally occurring proteins or synthetic polypeptide fragments).

The term "halo" refers to any radical of fluorine, chlorine, bromine or iodine. The term "alkyl" refers to a hydrocarbon chain that may be a straight chain or branched chain, containing the indicated number of carbon atoms. For example, $C_1$-$C_{10}$ indicates that the group may have from 1 to 10 (inclusive) carbon atoms in it. In the absence of any numerical designation, "alkyl" is a chain (straight or branched) having 1 to 20 (inclusive) carbon atoms in it. The term "alkylene" refers to a divalent alkyl (i.e., —R—).

The term "alkenyl" refers to a hydrocarbon chain that may be a straight chain or branched chain having one or more carbon-carbon double bonds. The alkenyl moiety contains the indicated number of carbon atoms. For example, $C_2$-$C_{10}$ indicates that the group may have from 2 to 10 (inclusive) carbon atoms in it. The term "lower alkenyl" refers to a $C_2$-$C_8$ alkenyl chain. In the absence of any numerical designation, "alkenyl" is a chain (straight or branched) having 2 to 20 (inclusive) carbon atoms in it.

The term "alkynyl" refers to a hydrocarbon chain that may be a straight chain or branched chain having one or more carbon-carbon triple bonds. The alkynyl moiety contains the indicated number of carbon atoms. For example, $C_2$-$C_{10}$ indicates that the group may have from 2 to 10 (inclusive) carbon atoms in it. The term "lower alkynyl" refers to a $C_2$-$C_8$ alkynyl chain. In the absence of any numerical designation, "alkynyl" is a chain (straight or branched) having 2 to 20 (inclusive) carbon atoms in it.

The term "aryl" refers to a 6-carbon monocyclic or 10-carbon bicyclic aromatic ring system wherein 0, 1, 2, 3, or 4 atoms of each ring may be substituted by a substituent. Examples of aryl groups include phenyl, naphthyl and the like. The term "arylalkyl" or the term "aralkyl" refers to alkyl substituted with an aryl. The term "arylalkoxy" refers to an alkoxy substituted with aryl.

The term "cycloalkyl" as employed herein includes saturated and partially unsaturated cyclic hydrocarbon groups having 3 to 12 carbons, preferably 3 to 8 carbons, and more preferably 3 to 6 carbons, wherein the cycloalkyl group additionally may be optionally substituted. Preferred cycloalkyl groups include, without limitation, cyclopropyl, cyclobutyl, cyclopentyl, cyclopentenyl, cyclohexyl, cyclohexenyl, cycloheptyl, and cyclooctyl.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring may be substituted by a substituent. Examples of heteroaryl groups include pyridyl, furyl or furanyl, imidazolyl, benzimidazolyl, pyrimidinyl, thiophenyl or thienyl, quinolinyl, indolyl, thiazolyl, and the like. The term "heteroarylalkyl" or the term "heteroaralkyl" refers to an alkyl substituted with a heteroaryl. The term "heteroarylalkoxy" refers to an alkoxy substituted with heteroaryl.

The term "heterocyclyl" refers to a nonaromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring may be substituted by a substituent. Examples of heterocyclyl groups include piperazinyl, pyrrolidinyl, dioxanyl, morpholinyl, tetrahydrofuranyl, and the like.

The term "substituents" refers to a group "substituted" on an alkyl, cycloalkyl, aryl, heterocyclyl, or heteroaryl group at any atom of that group. Suitable substituents include, without limitation, halo, hydroxy, mercapto, oxo, nitro, haloalkyl, alkyl, alkaryl, aryl, aralkyl, alkoxy, thioalkoxy, aryloxy, amino, alkoxycarbonyl, amido, carboxy, alkanesulfonyl, alkylcarbonyl, and cyano groups.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 1 depicts MAML polypeptides and locations for modification, shown as underlined (SEQ ID NOs: 19-20).

FIG. 3 depicts certain MAML polypeptides used in studies described herein. SEQ ID NOs:32-45 are shown in bold. MAML polypeptides containing the bolded sequences are shown as SEQ ID NOs: 19-31 and 26, respectively.

FIG. 9 depicts the results of studies examining the binding of immobilized stapled and unstapled SAHN11 to ICN1.

FIG. 23 depicts the results of a study showing that SAHN1, but not SANN1-D n cause a decrease in transcription from a CSL-responsive endogenous genes in T-ALL cells.

FIG. 24 depicts the results of a study showing that SAHN1 can elicit an apoptotic response in T-ALL cells.

DETAILED DESCRIPTION

Described herein are internally cross-linked alpha helical domain polypeptides related to human MAML. The polypeptides include a tether between two non-natural amino acids, which tether significantly enhances the alpha helical secondary structure of the polypeptide. Generally, the tether or cross-link (sometimes referred to as staple) extends across the length of one or two helical turns (i.e., about 3.4 or about 7 amino acids). Accordingly, amino acids positioned at i and i+3; i and i+4; or i and i+7 are ideal candidates for chemical modification and cross-linking. Thus, for example, where a peptide has the sequence . . . $Xaa_1$, $Xaa_2$, $Xaa_3$, $Xaa_4$, $Xaa_5$, $Xaa_6$, $Xaa_7$, $Xaa_8$, $Xaa_9$ . . . (wherein " . . . " indicates the optional presence of additional amino acids), cross-links between $Xaa_1$ and $Xaa_4$, or between $Xaa_1$ and $Xaa_5$, or between $Xaa_1$ and $Xaa_8$ are useful as are cross-links between $Xaa_2$ and $Xaa_5$, or between $Xaa_2$ and $Xaa_6$, or between $Xaa_2$ and $Xaa_9$, etc. The polypeptides can include more than one crosslink within the polypeptide sequence to either further stabilize the sequence or facilitate the stabilization of longer polypeptide stretches. If the polypeptides are too long to be readily synthesized in one part, independently synthesized cross-linked peptides can be conjoined by a technique called native chemical ligation (Bang, et al., *J. Am. Chem. Soc.* 126:1377).

The novel cross-linked polypeptides are useful, for example, to mimic or study proteins or polypeptides having one or more alpha-helical domains.

Figure 2:
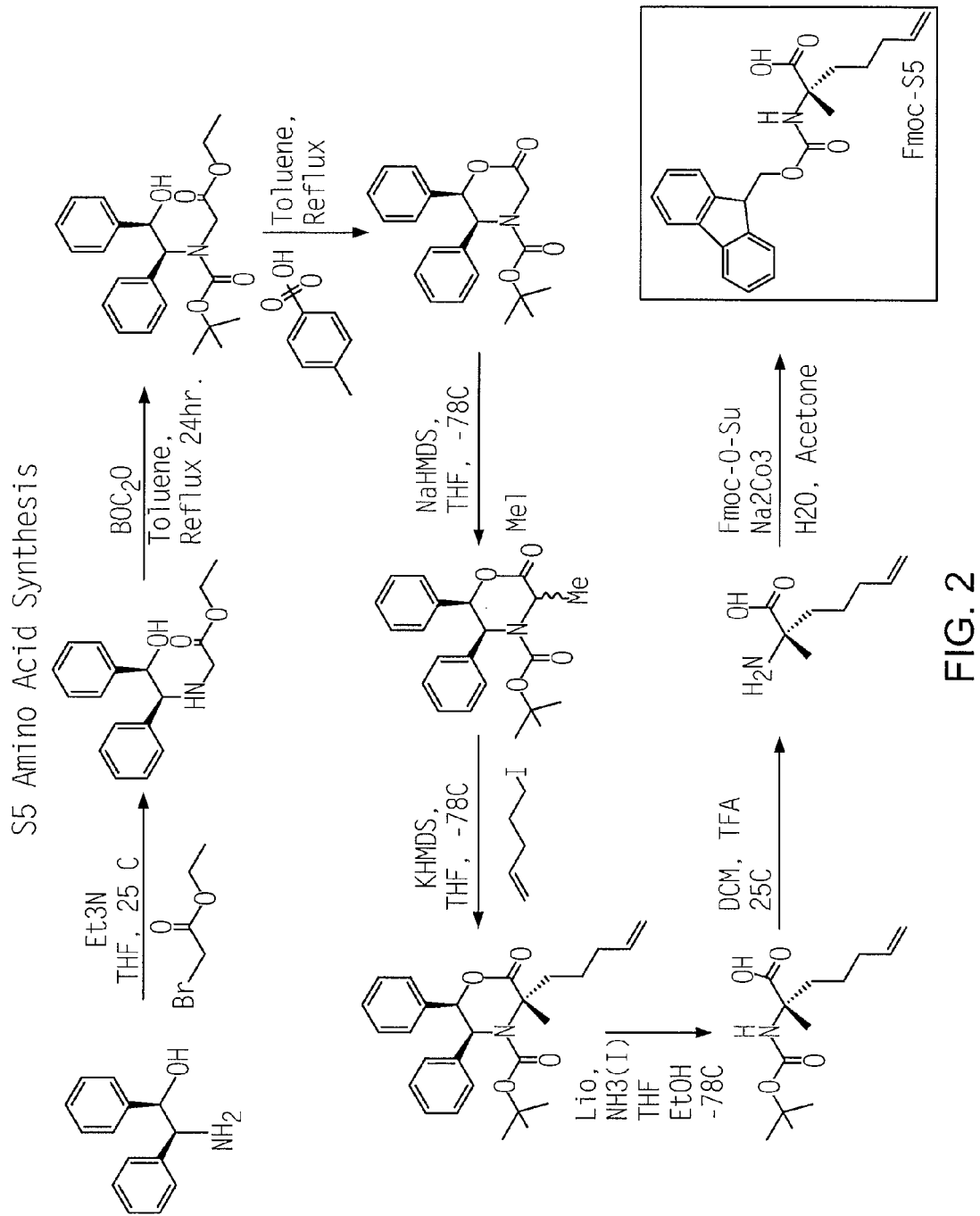
FIG. 2 depicts a synthetic strategy for the generation of α,α-disubstituted non-natural amino acids containing olefinic side chains.

Analysis conserved residues among MAML-1, 2 and 3; analysis of the predicted interaction between MAML and Notch; and analysis of predicted alpha-helical regions led to the identification amino acids that might be replaced to provide a cross-link without significantly inhibiting binding to Notch. Thus, as shown in FIG. 2 for MAML-1, residues that might be cross-linked are doubled underlined. Substitutions can be made at discrete locations, namely the "i, and i+4 positions" or the "i, and i+7 positions" shown for each phase (1 to 6) which facilitate cross-linking chemistry by placing reactive residues on the same face of the α-helix. Highly conserved amino acids among MAML polypeptides and those thought be important in protein-protein interactions based on X-ray crystallographic, are preferably not replaced. In FIG. 2 residues where changes are expected to be tolerated are single underlined. In certain circumstances, conserved amino acids can be replaced by other amino acids (e.g., synthetic non-naturally occurring amino acids).

α,α-Disubstituted non-natural amino acids containing olefinic side chains of varying length can synthesized by known methods (Williams et al. 1991 *J. Am. Chem. Soc.* 113:9276; Schafmeister et al. 2000 *J. Am. Chem. Soc.* 122:5891). FIG. 2 is a schematic depiction of the preparation of the non-natural amino acid (Fmoc-S5) used in solid phase peptide synthesis (SPPS) of i linked to i+4 peptides (one turn of the alpha helix is stabilized). For peptides where an i linked to i+7 staple is used (two turns of the helix stabilized) one S5 amino acid is used and one R8 is used. R8 is synthesized using the same route, except that the starting chiral auxiliary confers the R-alkyl-stereoisomer. Also, 8-iodooctene is used in place of 5-iodopentene. Inhibitors are synthesized on a solid support using solid-phase peptide synthesis (SPPS) on MBHA resin. Non-natural amino acids were synthesized by Moellering for incorporation into the final peptide product.

Various internally cross-linked peptides (REM-G1 to REM-G13, also called SAHN1 to SAHN13, respectively) shown in FIG. 3 were produced (X is a modified amino acid forming a cross-link). The underlined portions indicate the extent of each polypeptide, and the remainder of the MAML-1 sequence in each case is provided for context.

Figure 4A:
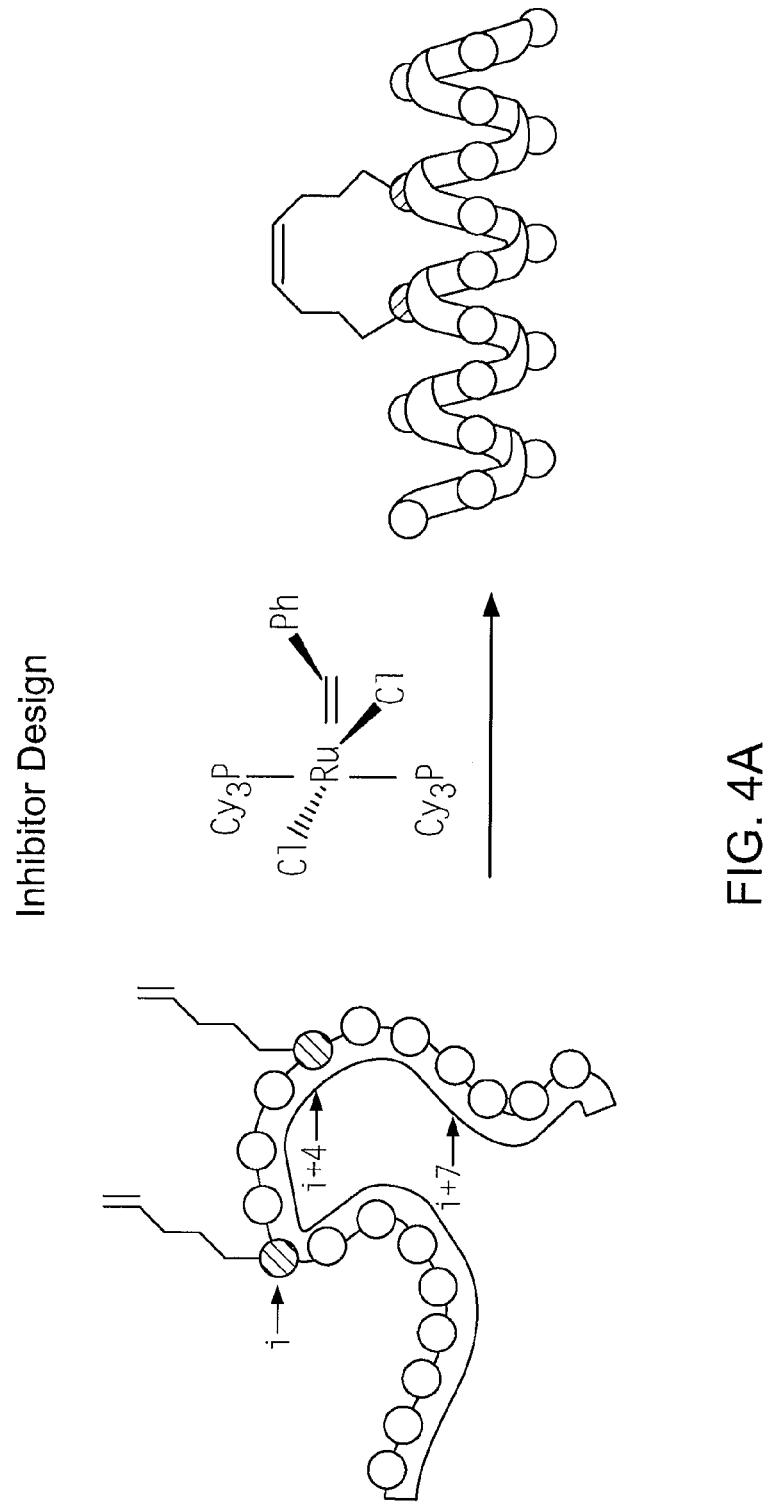
FIG. 4 depicts a stapled MAML polypeptide.
Figure 4B:
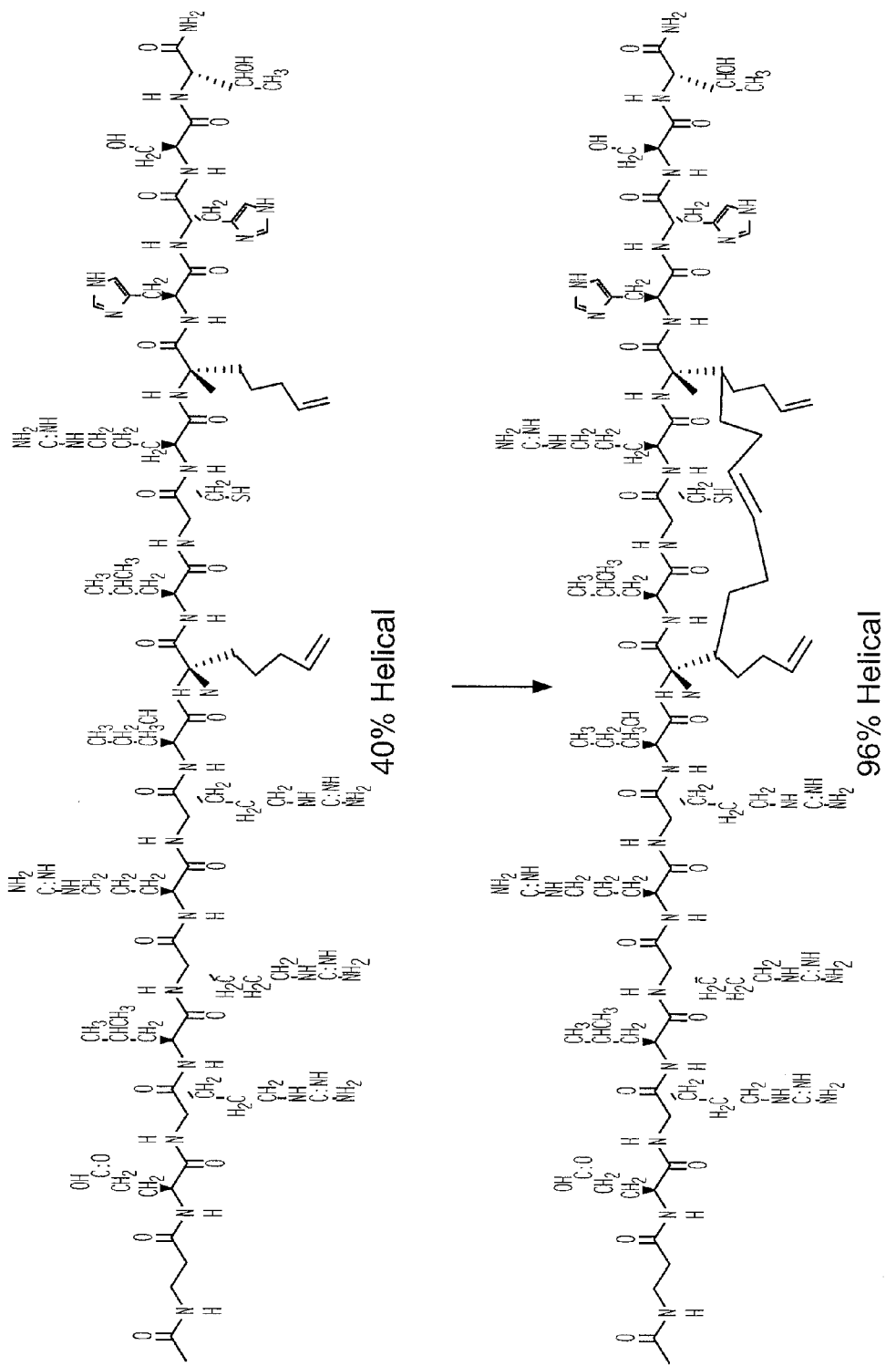
Figure 5:
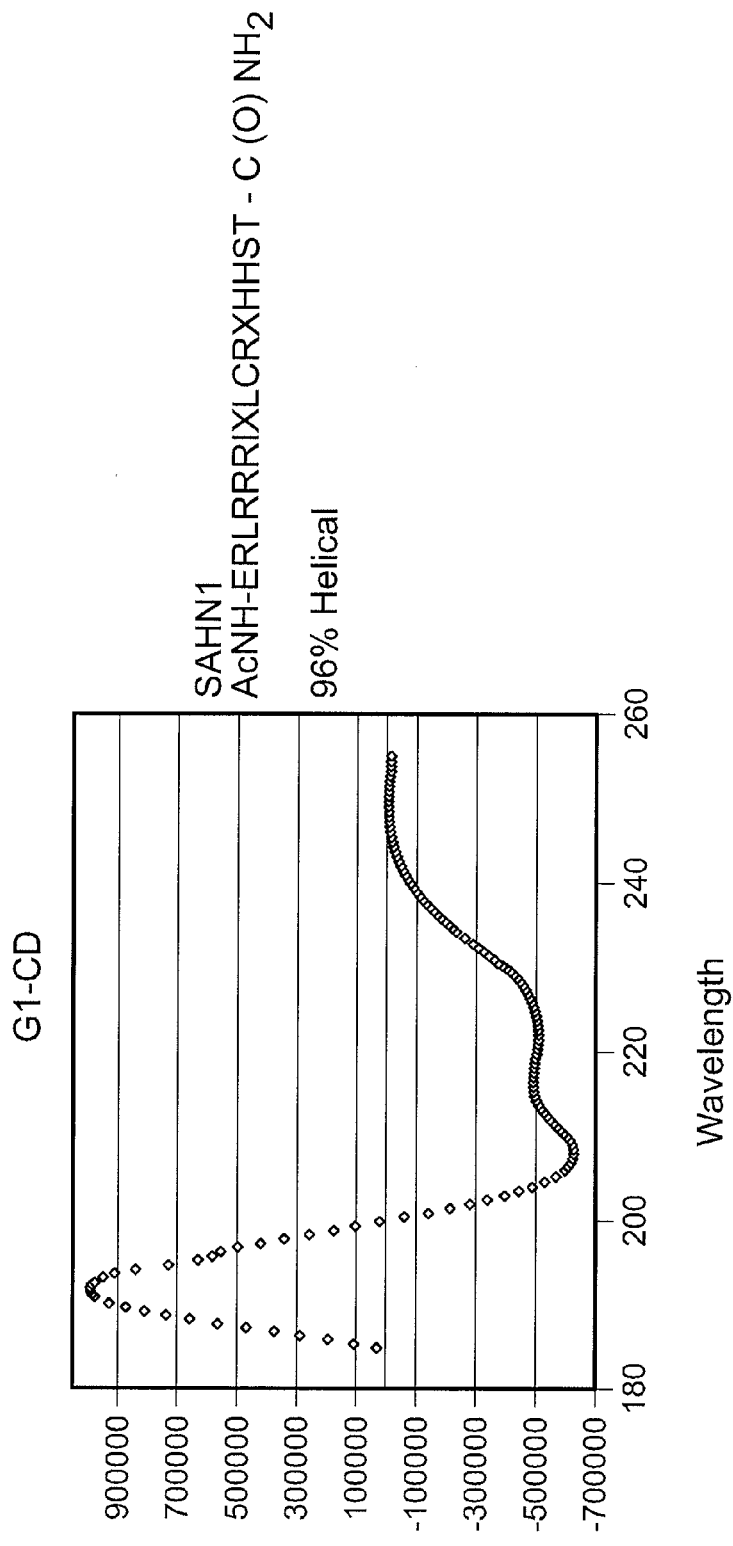
FIG. 5 depicts a CD spectra of a stapled polypeptide (SEQ ID NO: 34).
Figure 6A:
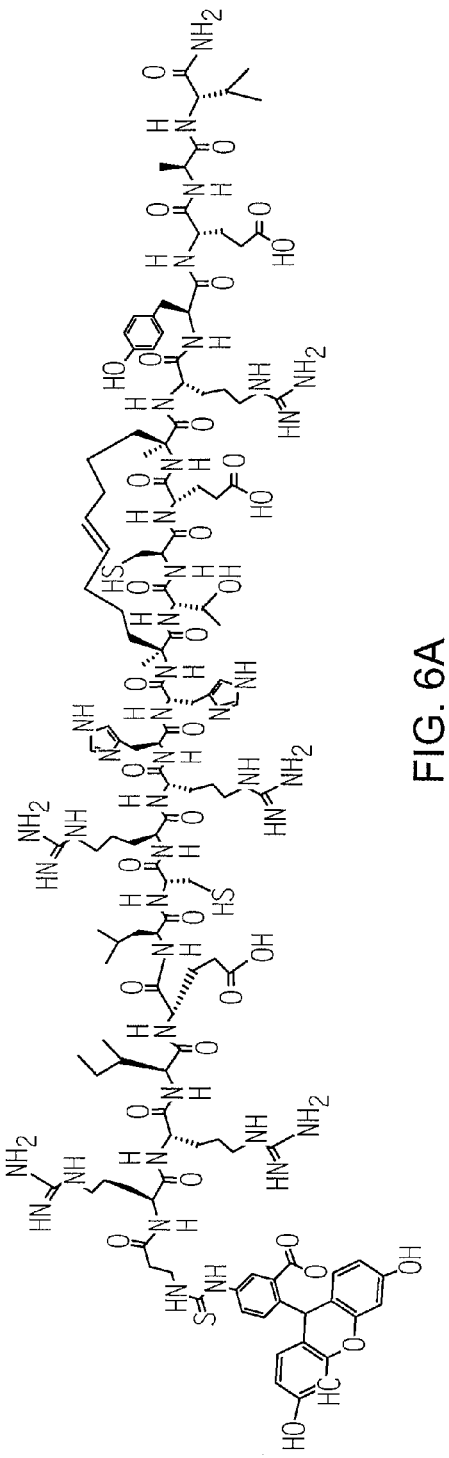
FIG. 6 depicts stapled MAML polypeptides.
Figure 6B:
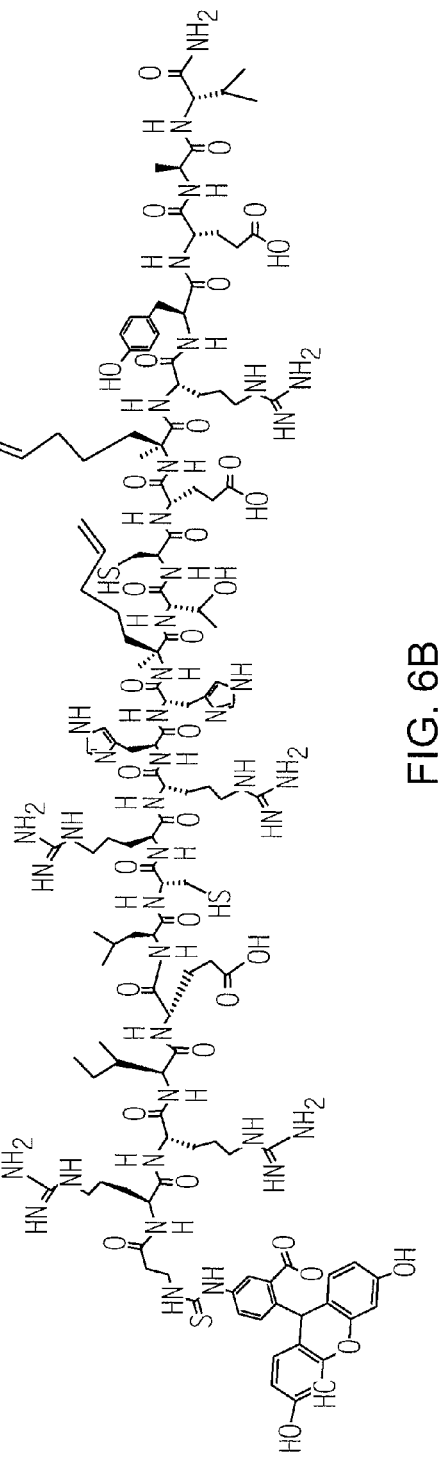
Figure 6C:
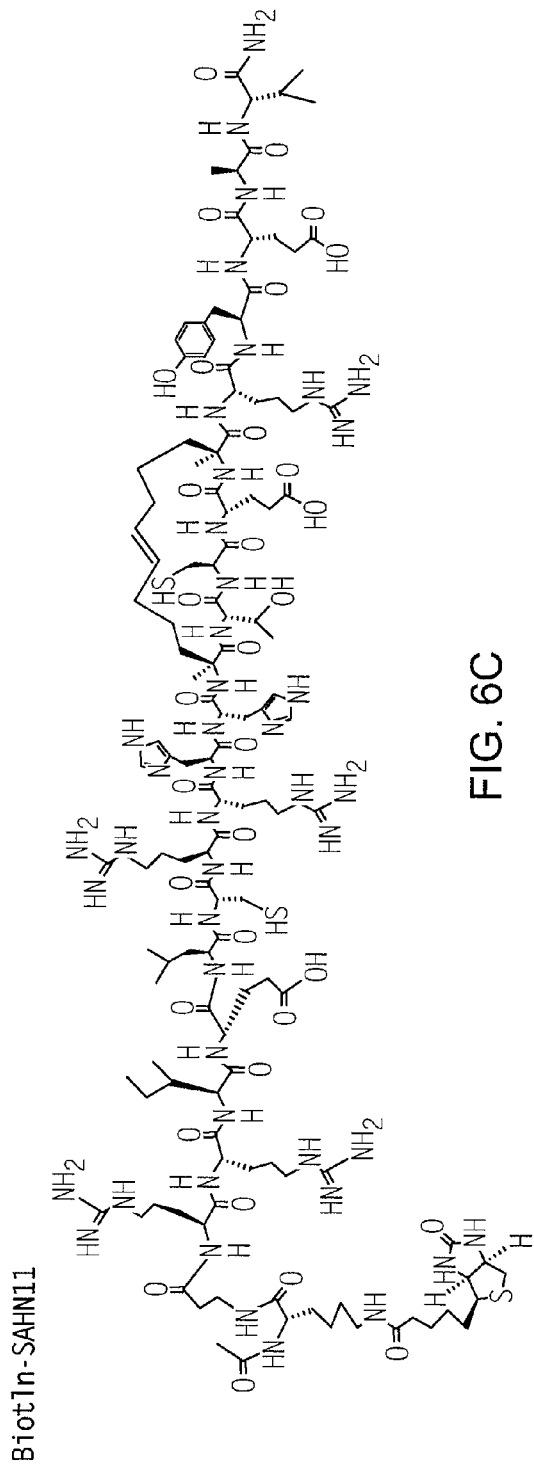

FIG. 4 is a schematic drawing and detailed structural depiction of a modified polypeptide having the sequence of REM-G1 (SAHN1). As seen in the circular dichromism spectra of FIG. 5, the modified polypeptide can be 96% alpha helical as compared to 40% when not cross-linked. FIG. 6 shows the detailed structure of versions of the modified, internally cross-linked polypeptide REM-G11 (SAHN11) that include either biotin or FITC labels.

Figure 7B:
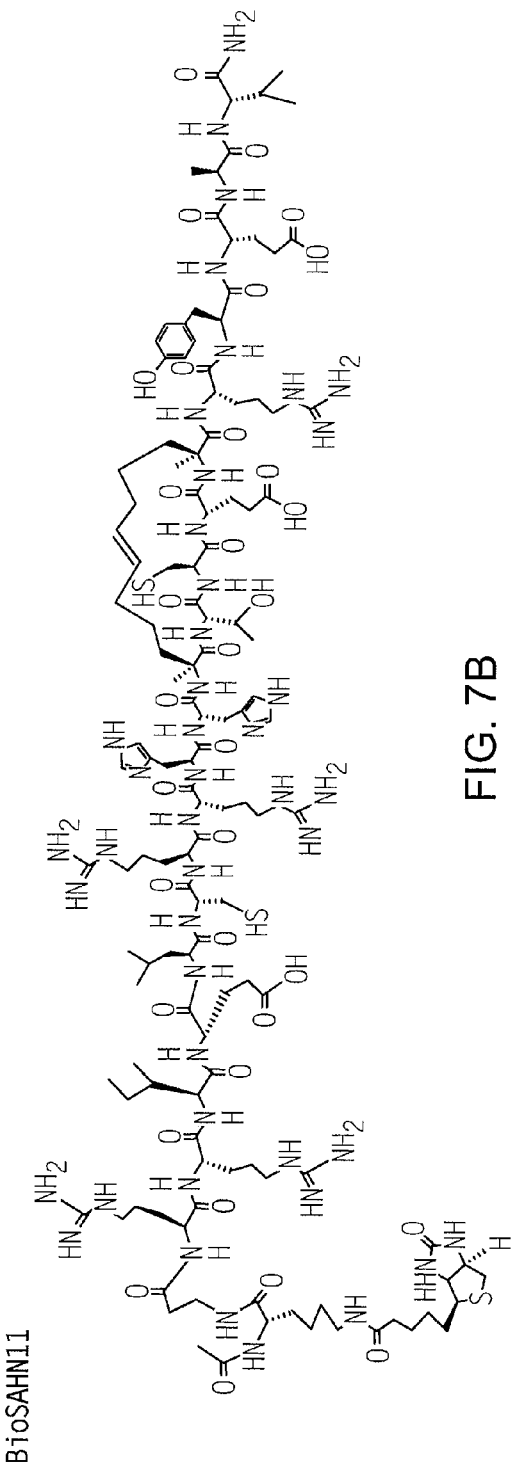
FIG. 7 depicts the results of surface plasmon resonance showing that BioSAHN11 binds ICN in a dose dependent manner.
Figure 7A:
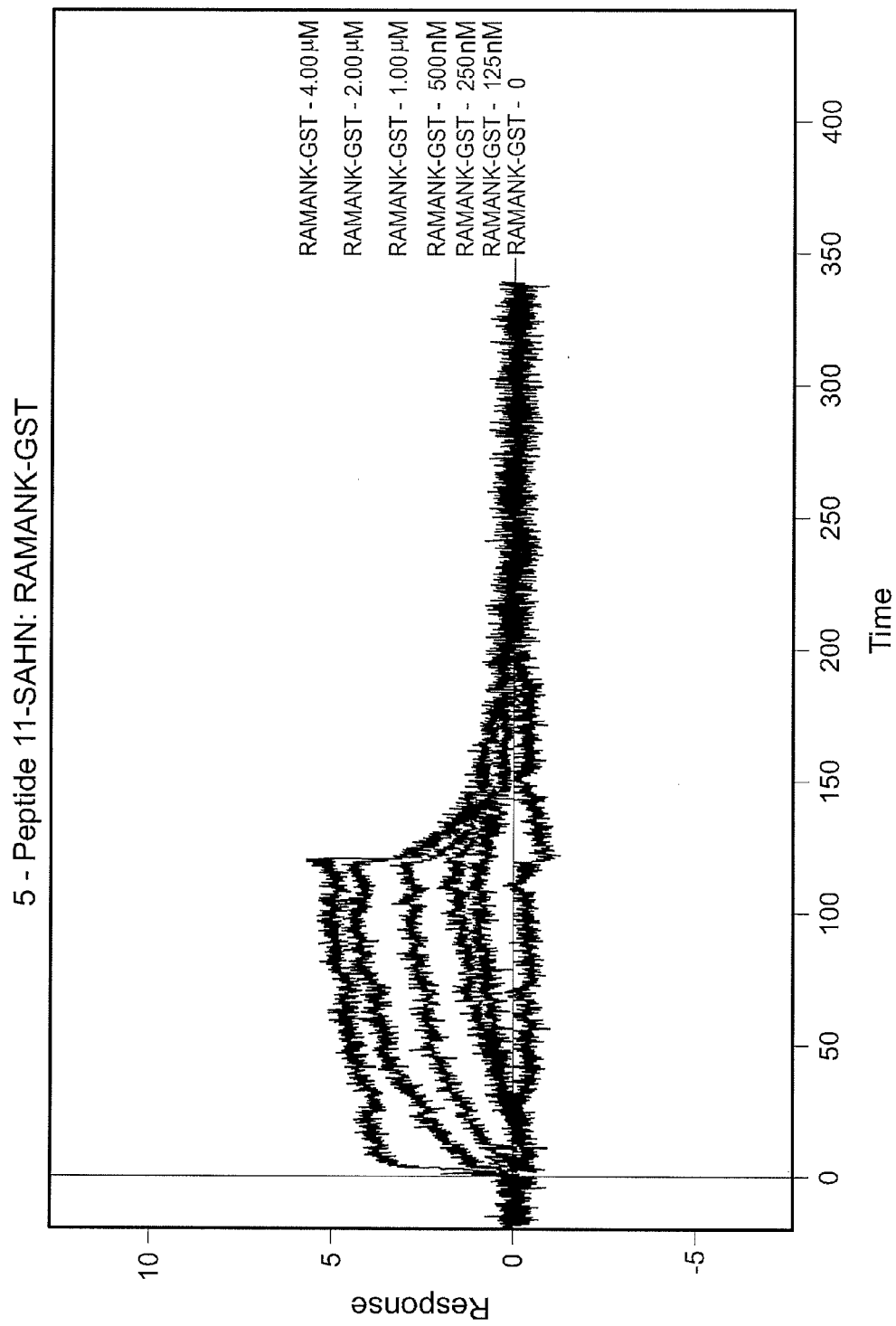

Surface plasmon resonance was used to demonstrated that the biotin-labeled cross-linker version of REM-G11 (Bio-SAHN11) binds ICN in a dose dependent manner (FIG. 7).

Biochemical association between stapled peptides and the Notch complex was also investigated using surface plasmon resonance. These studies employed immobilized ICN protein (an anti-GST antibody and a GST-tagged, purified ICN protein comprising the RAM and ANK domains). Other studies employed biotinylated stapled peptides and a streptavidin-functionalized sensor surface.

Figure 8A:
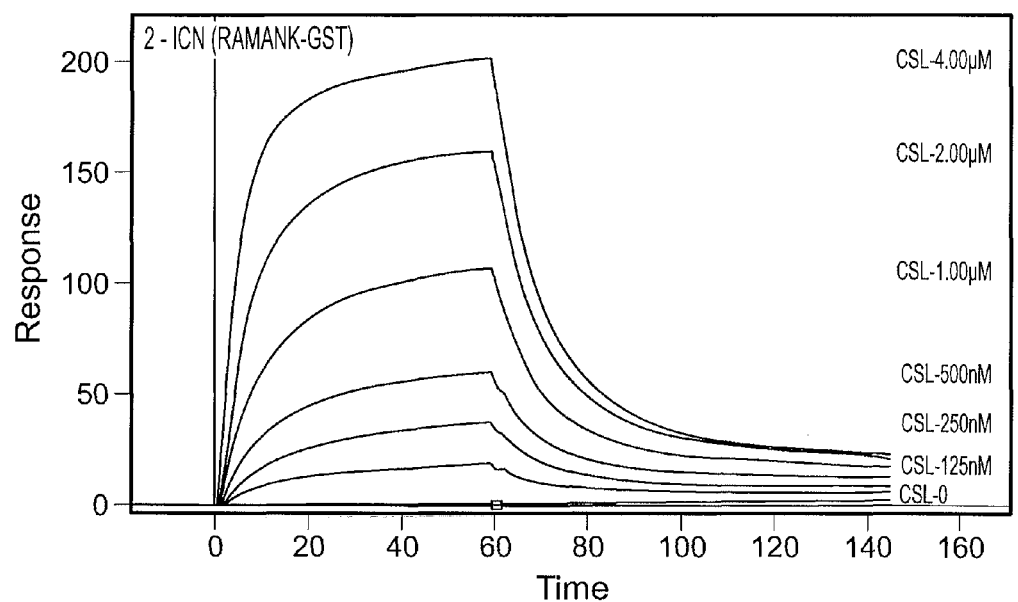
FIG. 8 depicts the results of surface plasmon resonance showing that immobilized ICN associates with CSL in a dose-dependent manner.
Figure 8B:
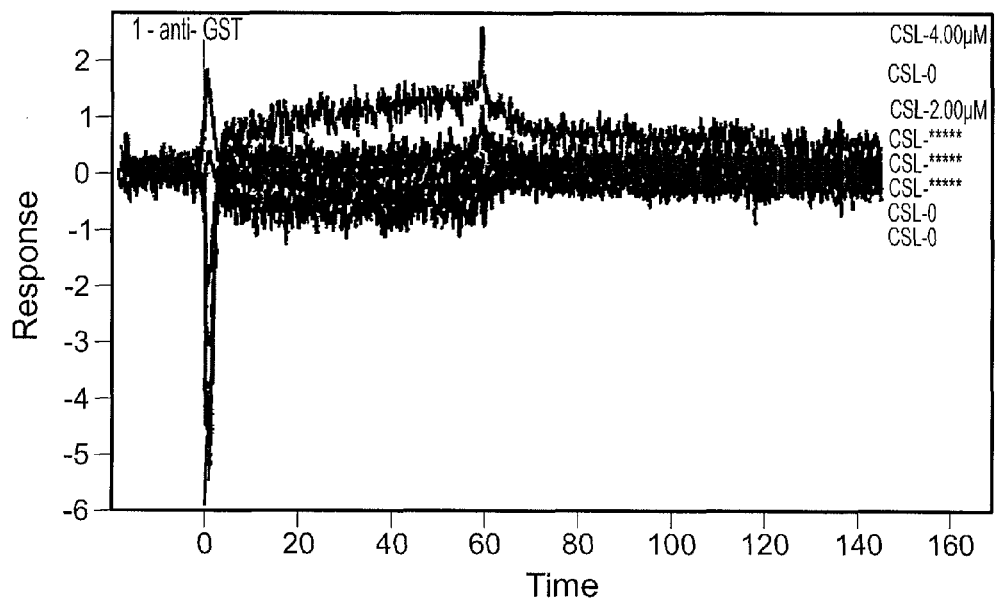

We demonstrated that immobilized ICN associates with CSL in a dose-dependent manner. The association exhibited a two-phase kinetic association, first with RAM binding and subsequently with a lower-affinity association with the ANK domain (see FIG. 8). Non-specific binding to a reference surface with anti-GST antibody was only minimal.

Binding of immobilized stapled and unstapled SAHN11 to ICN1 demonstrated that stapled (cross-linked) SAHN11 binds ICN with greater affinity (Kd=0.96 µM) than non-stapled SAHN11 (Kd=2.63 µM) (FIG. 9).

Immunoprecipitation studies using MOLT4 cell lysates, ALL-SIL cell lysates and KOPTK1 cell lysates found that biotin labeled SAHN1 can be used to pull down ICN. A reverse immunoprecipitation assay using FITC labeled SAHN1 found that SAHN1 can be used to pull down ICN in MOLT4 cell lysates.

Figure 10:
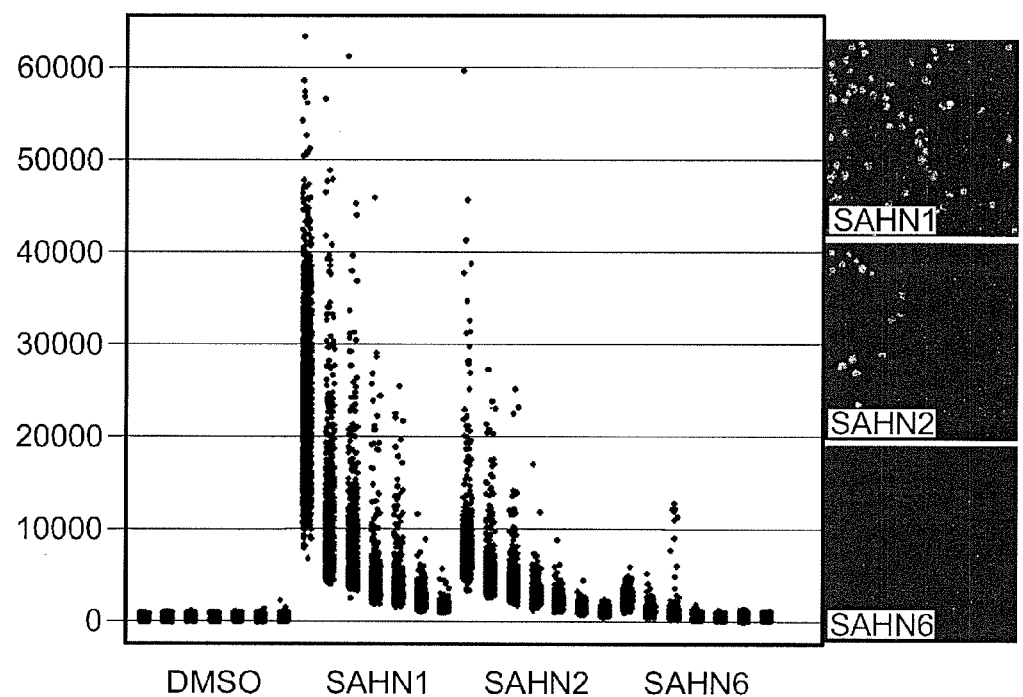
FIG. 10 depicts the results of studies on cellular uptake of SAHN1, SAHN2 and SAHN6.

Automated quantitative immunofluorescence was used to determine the intracellular distribution of fluorophore-labeled stapled alpha helices. Cells were incubated with FITC-conjugated peptides SAHN1, SAHN2, or SAHN6; or control. At 16 hours measurements of cellular fluorescence were taken using epifluorescence microscopy. The results of these studies are shown in FIG. 10 in which each circle represents an individual cell and each column represents a treatment condition. Both SAHN1 and SAHN2 exhibited significant intracellular passage, whereas SAHN6 did not.

Figure 11:
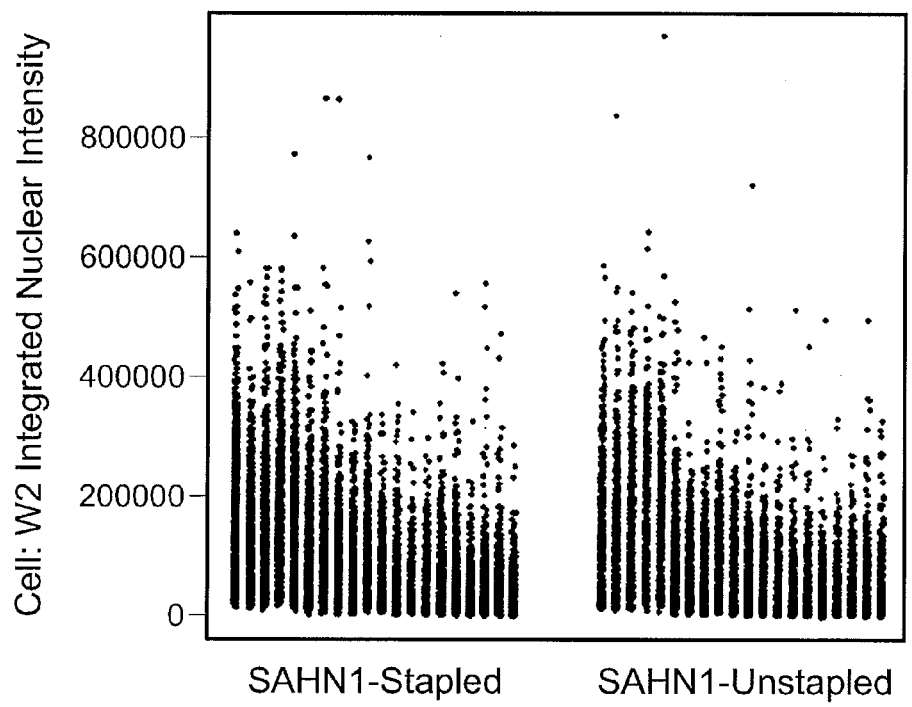
FIG. 11 depicts the results of studies on cellular uptake of stapled and unstapled SAHN1.

Automated quantitative immunofluorescence was also used to determine the intracellular distribution of fluorophore-labeled stapled alpha helices. Cells were incubated with FITC-conjugated peptides SAHN1, or unstapled SAHN1. As shown in FIG. 11, stapling of the peptide did not, in this instance, appear to impact intracellular passage.

Epifluorescence microscopy demonstrated that SAHN11 exhibits intracellular distribution. Confocal microscopy analysis suggested that both stapled and unstapled SAHN1 peptides appear to distribute to the intracellular compartment through endocytosis.

Figure 12:
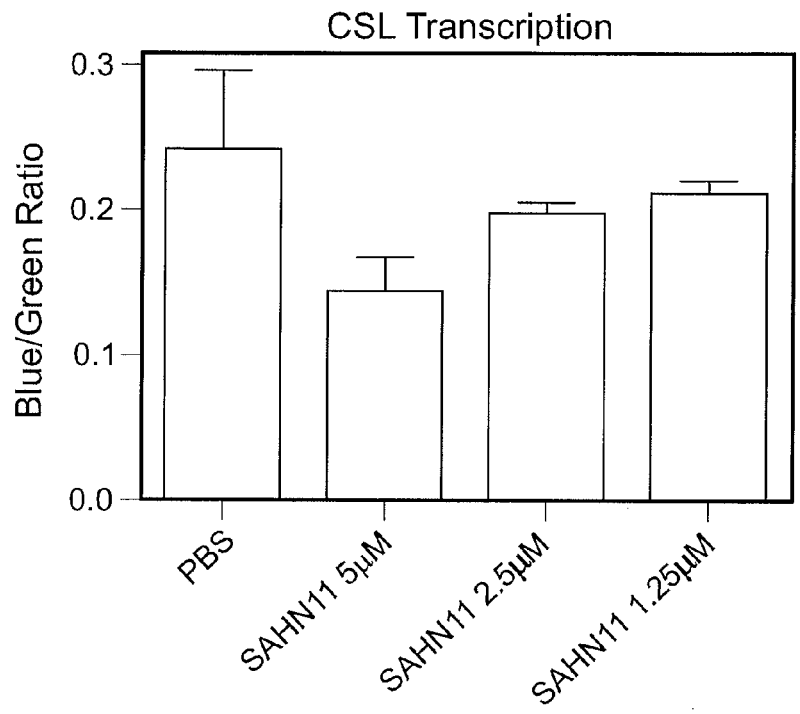
FIG. 12 depicts the results of a study showing that stapled SAHN11 reduces expression of the CSL-responsive reporter in a dose-dependent manner.

MOLT4 cells transfected with a CSL-responsive reporter were used to test whether stapled SAHN11 can interfere with Notch-mediated activation of transcription. As can be seen in FIG. 12, stapled SAHN11 reduced expression of the CSL-responsive reporter in a dose-dependent manner.

Figure 13:
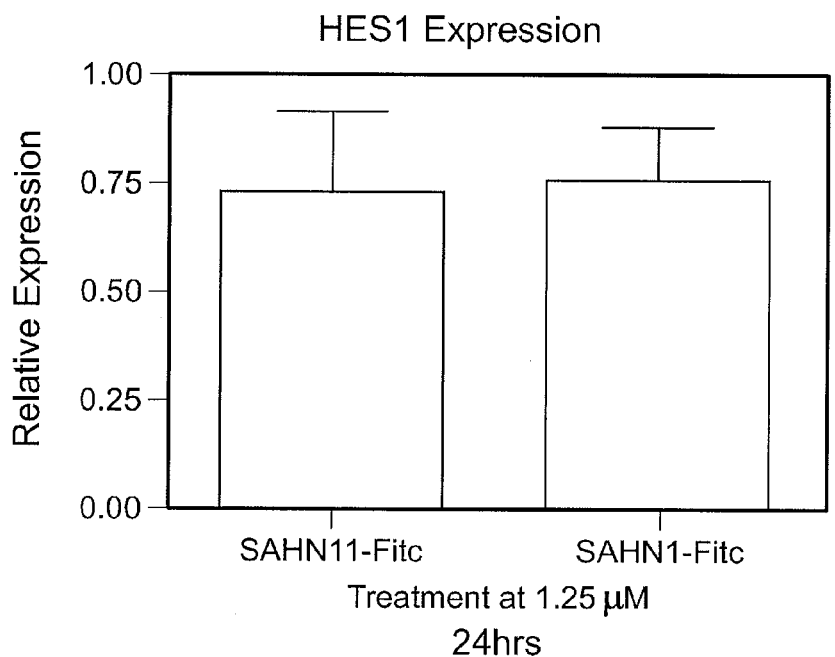
FIG. 13 depicts the results of a study showing that T-ALL1 cells exposed to either SAHN11-FITC or SAHN1-FITC exhibit reduced HES1 expression relative to expression of a housekeeping gene.

HES1 is Notch responsive gene. As shown in FIG. 13, T-ALL1 cells exposed to either SAHN11-FITC or SAHN1-FITC exhibit reduced HES1 expression relative to expression of a housekeeping gene (beta-actin).

Figure 14:
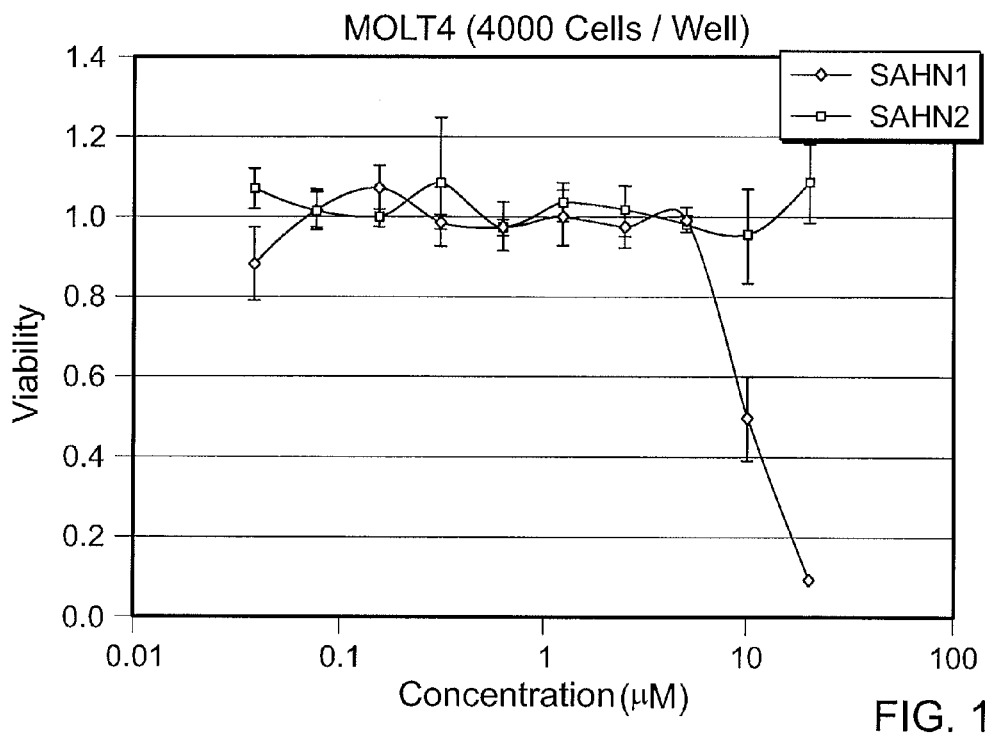
FIG. 14 depicts the results of a study showing that stapled SAHN2 reduces the viability of MOLT4 cells.
Figure 15:
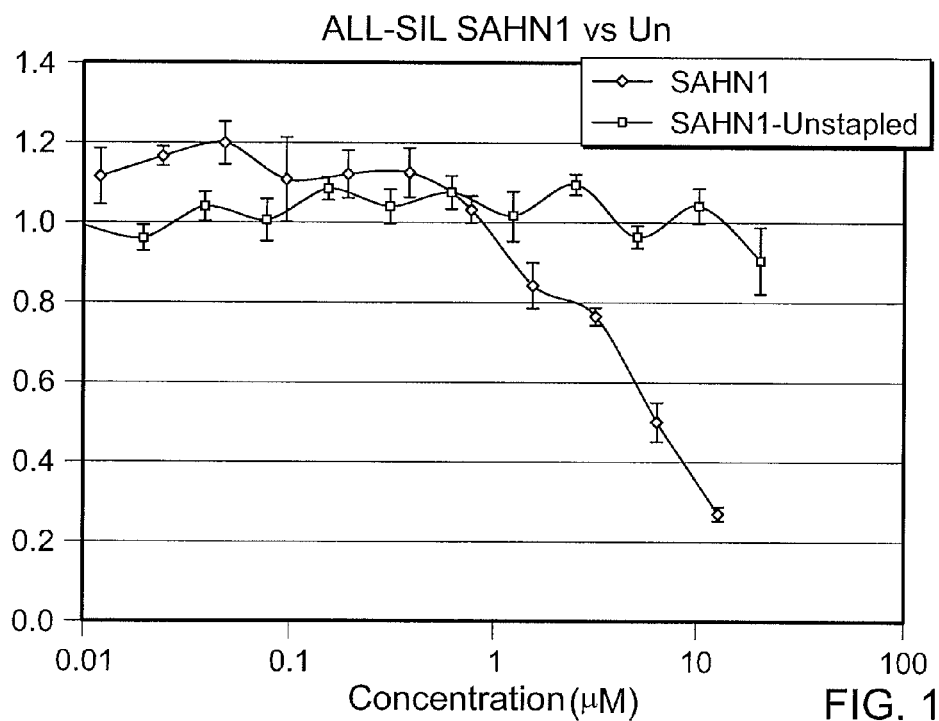
FIG. 15 depicts the results of a study showing that stapled SAHN1, but not unstapled SAHN1, reduces the viability of ALL-SIL cells.
Figure 16:
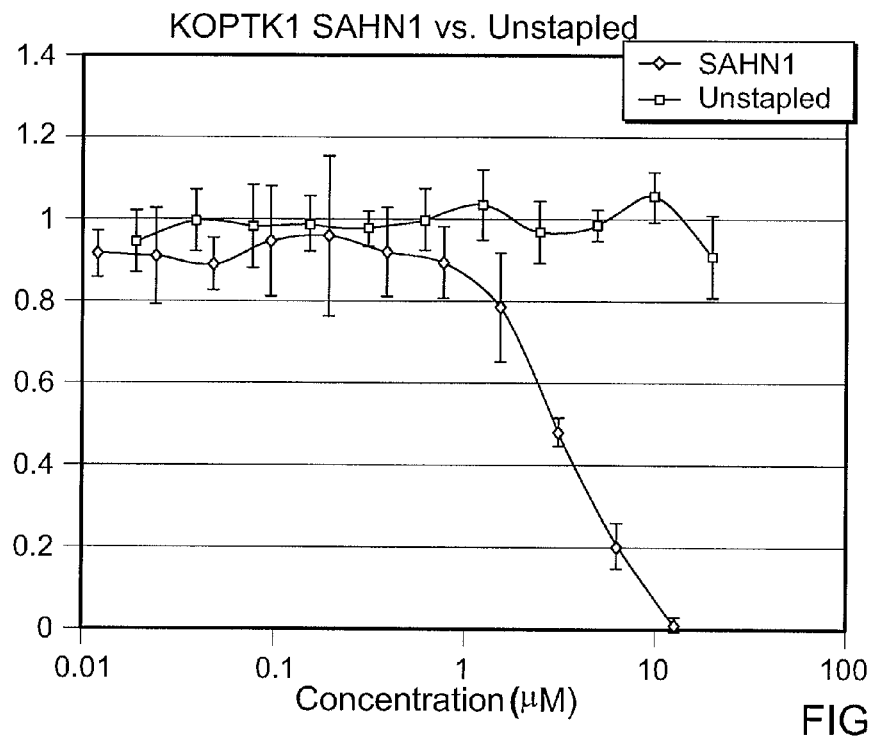
FIG. 16 depicts the results of a study showing that stapled SAHN1, but not unstapled SAHN1, reduces the viability of KOPTK1 cells.
Figure 17:
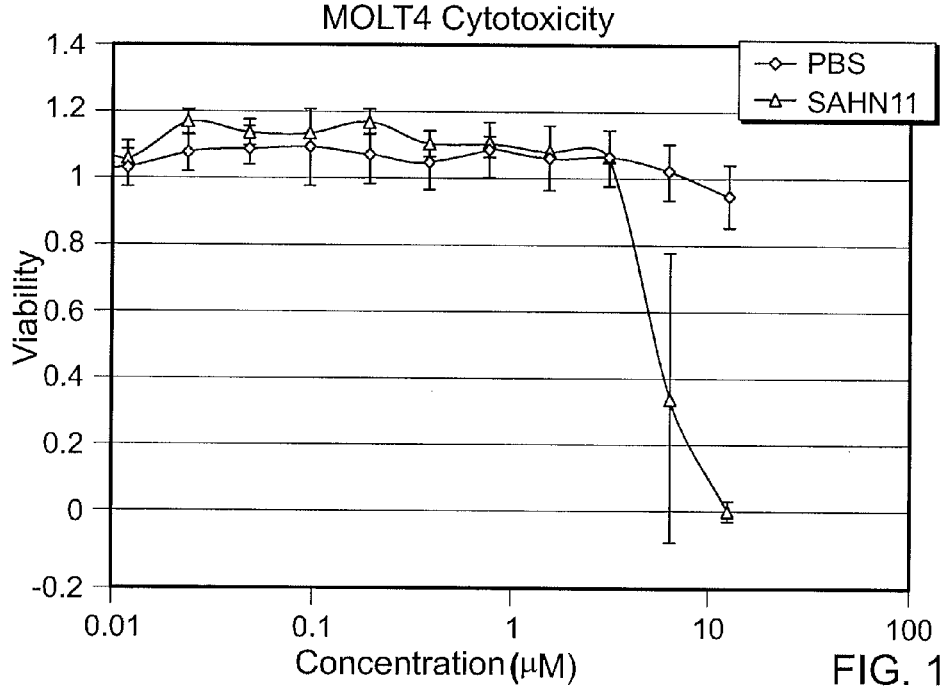
FIG. 17 depicts the results of a study showing that stapled SAHN11 reduces the viability of MOLT4 cells.
Figure 18:
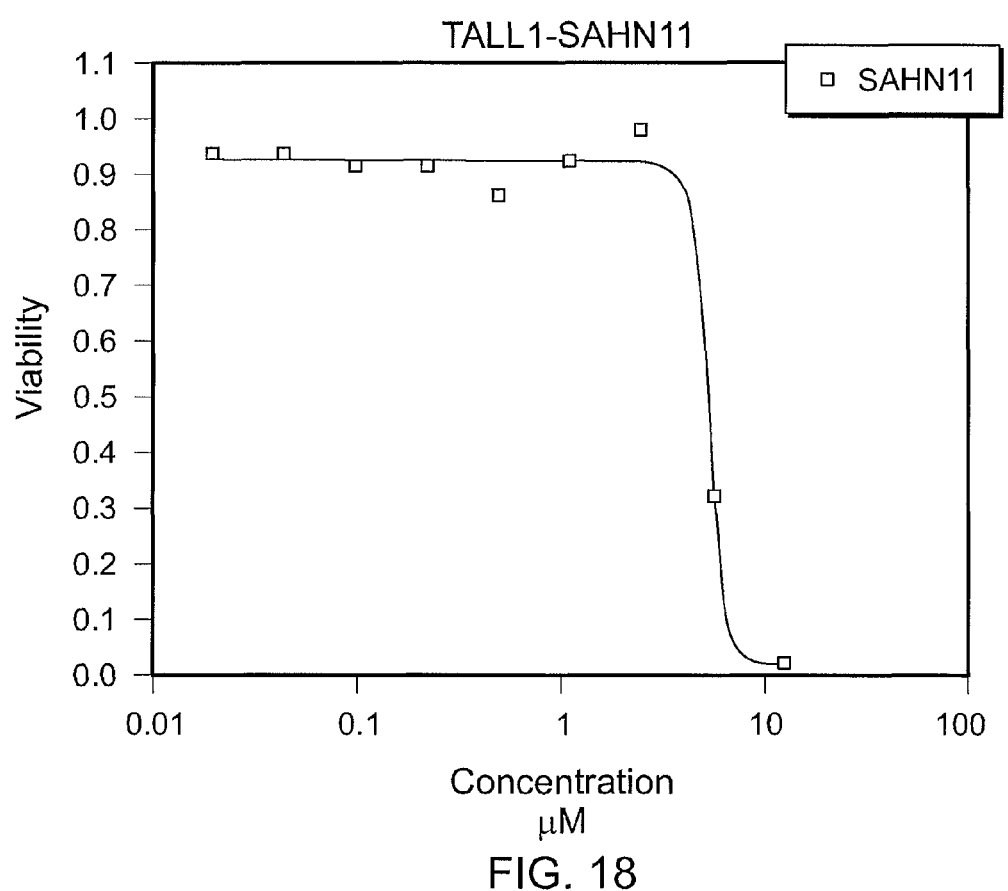
FIG. 18 depicts the results of a study showing that stapled SAHN11 reduces the viability of TALL1 cells.

As shown in FIG. 14, stapled SAHN2 reduced the viability of MOLT4 cells. As shown in FIG. 15, stapled SAHN1, but not unstapled SAHN1, reduced the viability of ALL-SIL cells. As shown in FIG. 16, stapled SAHN1, but not unstapled SAHN1, reduced the viability of KOPTK1 cells. As shown in FIG. 17, stapled SAHN11 reduced the viability of MOLT4 cells. As shown in FIG. 18, stapled SAHN11 reduced the viability of TALL1 cells.

Immobilized SAHN1 was used to measure the apparent Kd for a pre-assembled ICN-CSL complex by surface plasmon resonance. The result of this analysis revealed an apparent Kd of 98 nM.

A damaged variant of SAHN1 was created by changing the Glu indicated by * in the SAHN1 depicted in FIG. 6 to an Arg and changing the Arg indicated by + in the SAHN1 depicted in FIG. 6 to Glu. This damaged variant, which has the same net charge as SANN1, is referred to as SAHN1-D.

Immobilized SAHN1-D was used to measure the apparent Kd for a pre-assembled ICN-CSL complex by surface plasmon resonance. The result of this analysis revealed an apparent Kd of 1.40 µM.

Figure 19:
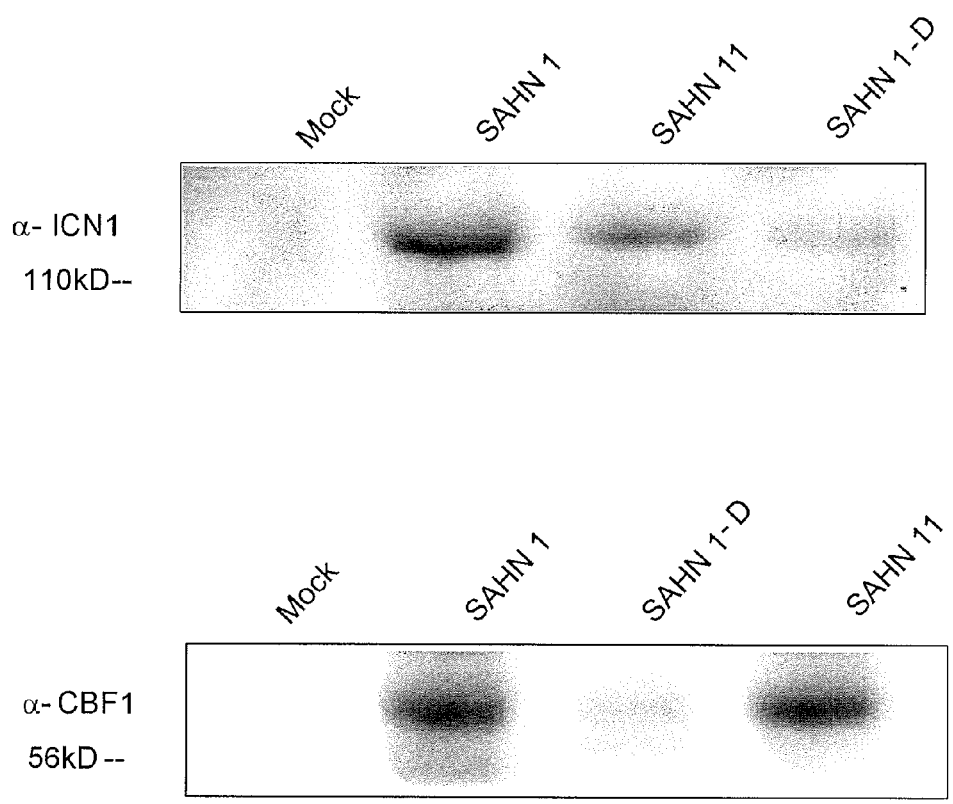
FIG. 19 depicts the results of a study showing that SAHN1, but not SAHN1-D can bind to ICN1/CSL in T-ALL cellular lysates.

Immunoprecipitation studies using T-ALL (KOPTK1) cell lysates demonstrated that SAHN1 and SAHN11, but not SAHN1-D, can pull down both ICN and CSL. The results of the analysis are shown in FIG. 19.

Figure 20:
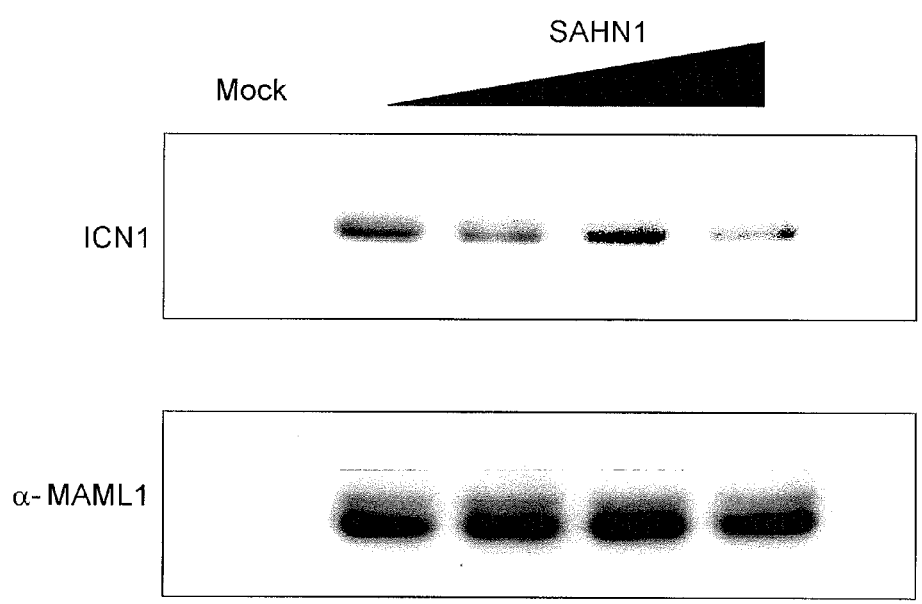
FIG. 20 depicts the results of a study showing that SAHN1 can compete off ICN1 bound to MAML in T-ALL cellular lysates.

A study using T-ALL cellular lysates found that SAHN1 can compete away ICN1 that is bound to immunoprecipitated MAML. The results of this analysis are shown in FIG. 20.

Figure 21:
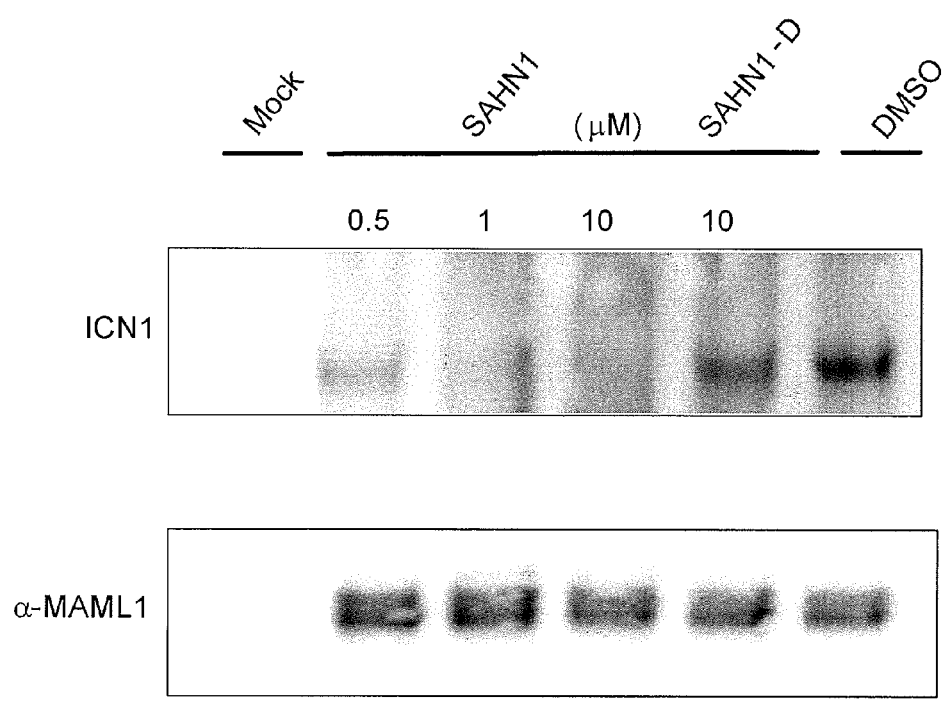
FIG. 21 depicts the results of a study showing that SAHN1-D cannot compete off ICN1 bound to MAML in T-ALL cellular lysates

A study using T-ALL cellular lysates found that SAHN1-D cannot effectively compete away ICN1 that is bound to immunoprecipitated MAML. The results of this analysis are shown in FIG. 21.

Figure 22:
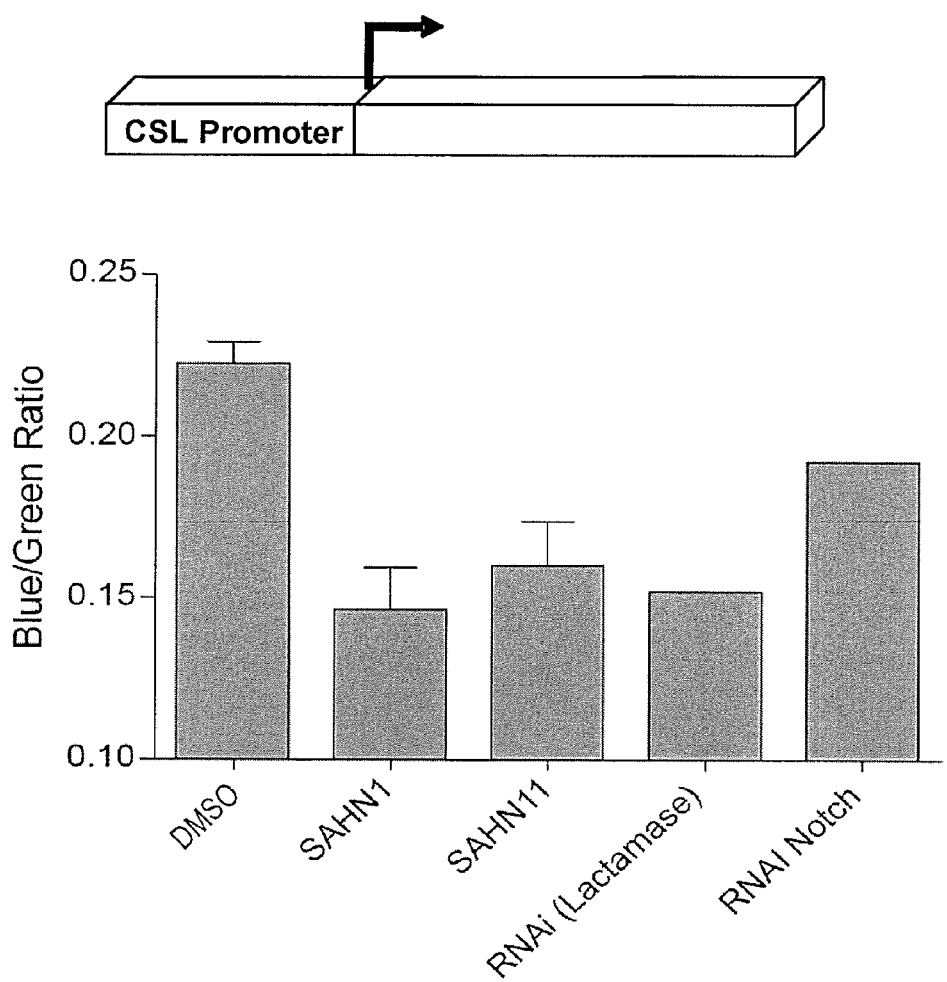
FIG. 22 depicts the results of a study showing that SAHN1 and SAHN11 can cause a decrease in transcription from a CSL-responsive reporter in T-ALL cells.

T-ALL cells (MOLT4) harboring a beta-lactamase gene under the control of a CSL responsive promoter was used to study the effect of SAHN1 and SAHN11 on Notch complex mediated transcription. This study found that both SAHN1 and SAHN11 decreased transcription and that the decrease was similar in magnitude to that caused by an RNAi directed against Notch and an RNAi directed against lactamase. The results of this analysis are shown in FIG. 22.

A study in T-ALL cells (MOLT4) found that SAHN1, but not SAHN1-D, decrease expression of HES1 and HEY1, both Notch-driven genes, in a dose dependent manner. The results of this analysis are show in FIG. 23.

A study in gamma secretase resistant T-ALL cells (MOLT4) found that SAHN1, but not SAHN1-D induces an apoptotic response after 24 or 48 hours. The results of this analysis are show in FIG. 24.

Figure 25:
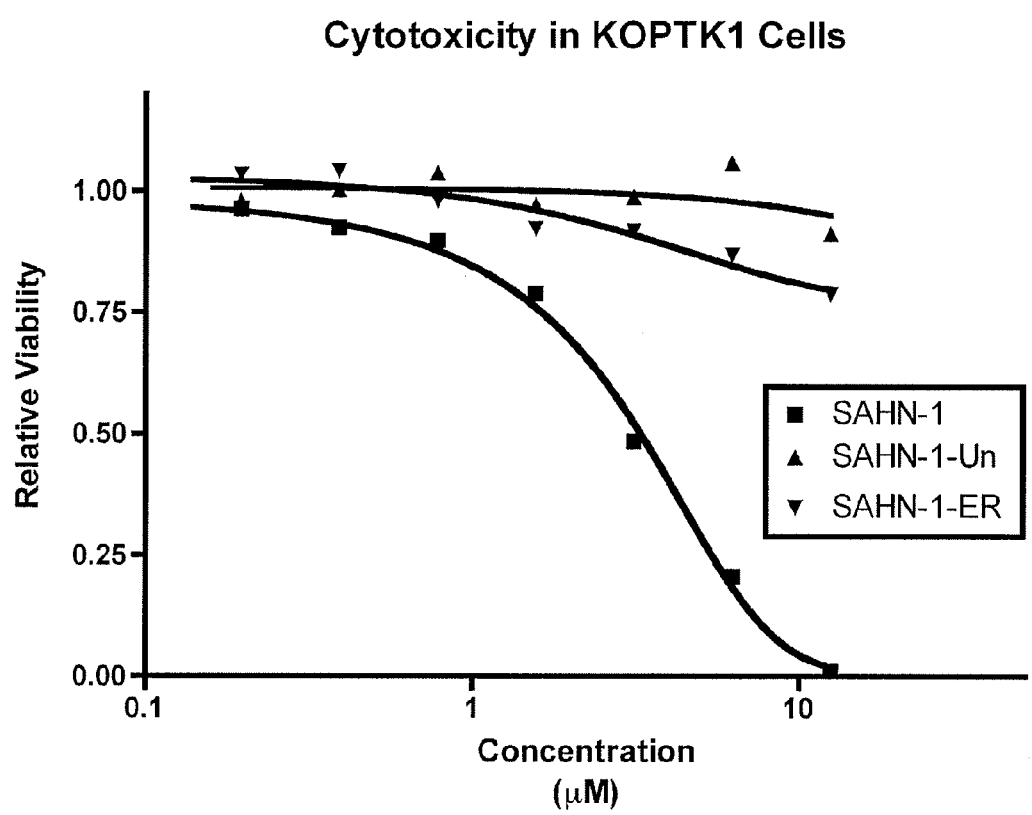
FIG. 25 depicts the results of a study showing that SAHN1 decreases the viability of MOLT4 T-ALL cells.

A study in T-ALL cells (KOPTK1) found that SAHN1 decreased cell viability ($IC_{50}$=8 µM). SAHN1-D had little effect on cell viability. The results of this analysis are show in FIG. 25.

Additional studies found that SAHN1, but not SAHN1-D, is cytotoxic to neoplastic murine lymphocytes derived from transgenic mice harboring the clinically relevant human Notch mutations (a L to P change at position 1601 and a PEST domain mutation).

Polypeptides

In some instances, the hydrocarbon tethers (i.e., cross links) described herein can be further manipulated. In one instance, a double bond of a hydrocarbon alkenyl tether, (e.g., as synthesized using a ruthenium-catalyzed ring closing metathesis (RCM)) can be oxidized (e.g., via epoxidation or dihydroxylation) to provide one of compounds below.

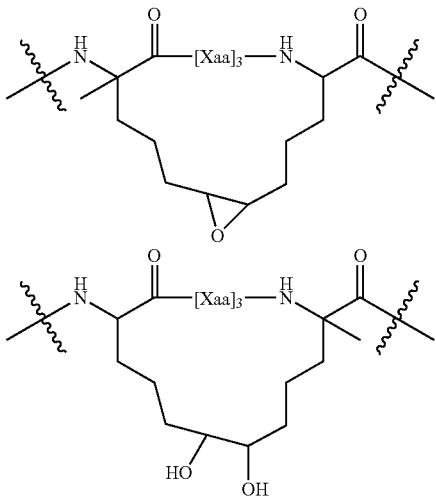

Either the epoxide moiety or one of the free hydroxyl moieties can be further functionalized. For example, the epoxide can be treated with a nucleophile, which provides additional functionality that can be used, for example, to attach a tag (e.g., a radioisotope or fluorescent tag). The tag can be used to help direct the compound to a desired location in the body or track the location of the compound in the body. Alternatively, an additional therapeutic agent can be chemically attached to the functionalized tether (e.g., an anti-cancer agent such as rapamycin, vinblastine, taxol, etc.). Such derivitization can alternatively be achieved by synthetic manipulation of the amino or carboxy terminus of the polypeptide or via the amino acid side chain. Other agents can be attached to the functionalized tether, e.g., an agent that facilitates entry of the polypeptide into cells.

While hydrocarbon tethers have been described, other tethers are also envisioned. For example, the tether can include one or more of an ether, thioether, ester, amine, or amide moiety. In some cases, a naturally occurring amino acid side chain can be incorporated into the tether. For example, a tether can be coupled with a functional group such as the hydroxyl in serine, the thiol in cysteine, the primary amine in lysine, the acid in aspartate or glutamate, or the amide in asparagine or glutamine. Accordingly, it is possible to create a tether using naturally occurring amino acids rather than using a tether that is made by coupling two non-naturally occurring amino acids. It is also possible to use a single non-naturally occurring amino acid together with a naturally occurring amino acid.

It is further envisioned that the length of the tether can be varied. For instance, a shorter length of tether can be used where it is desirable to provide a relatively high degree of constraint on the secondary alpha-helical structure, whereas, in some instances, it is desirable to provide less constraint on the secondary alpha-helical structure, and thus a longer tether may be desired.

Additionally, while examples of tethers spanning from amino acids i to i+3, i to i+4; and i to i+7 have been described in order to provide a tether that is primarily on a single face of the alpha helix, the tethers can be synthesized to span any combinations of numbers of amino acids.

In some instances, alpha disubstituted amino acids are used in the polypeptide to improve the stability of the alpha helical secondary structure. However, alpha disubstituted amino acids are not required, and instances using mono-alpha substituents (e.g., in the tethered amino acids) are also envisioned.

As can be appreciated by the skilled artisan, methods of synthesizing the compounds of the described herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, Comprehensive Organic Transformations, VCH Publishers (1989); T. W. Greene and P. G. M. Wuts, Protective Groups in Organic Synthesis, 2d. Ed., John Wiley and Sons (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

The peptides of this invention can be made by chemical synthesis methods, which are well known to the ordinarily skilled artisan. See, for example, Fields et al., Chapter 3 in Synthetic Peptides: A User's Guide, ed. Grant, W.H. Freeman & Co., New York, N.Y., 1992, p. 77. Hence, peptides can be synthesized using the automated Merrifield techniques of solid phase synthesis with the α-NH$_2$ protected by either t-Boc or F-moc chemistry using side chain protected amino acids on, for example, an Applied Biosystems Peptide Synthesizer Model 430A or 431.

One manner of making of the peptides described herein is using solid phase peptide synthesis (SPPS). The C-terminal amino acid is attached to a cross-linked polystyrene resin via an acid labile bond with a linker molecule. This resin is insoluble in the solvents used for synthesis, making it relatively simple and fast to wash away excess reagents and by-products. The N-terminus is protected with the Fmoc group, which is stable in acid, but removable by base. Any side chain functional groups are protected with base stable, acid labile groups.

Longer peptides could be made by conjoining individual synthetic peptides using native chemical ligation. Alternatively, the longer synthetic peptides can be synthesized by well known recombinant DNA techniques. Such techniques are provided in well-known standard manuals with detailed protocols. To construct a gene encoding a peptide of this invention, the amino acid sequence is reverse translated to obtain a nucleic acid sequence encoding the amino acid sequence, preferably with codons that are optimum for the organism in which the gene is to be expressed. Next, a synthetic gene is made, typically by synthesizing oligonucleotides which encode the peptide and any regulatory elements, if necessary. The synthetic gene is inserted in a suitable cloning vector and transfected into a host cell. The peptide is then expressed under suitable conditions appropriate for the selected expression system and host. The peptide is purified and characterized by standard methods.

The peptides can be made in a high-throughput, combinatorial fashion, e.g., using a high-throughput multiple channel combinatorial synthesizer available from Advanced Chemtech. In the modified polypeptides one or more conventional peptide bonds replaced by an a different bond that may increase the stability of the polypeptide in the body. Peptide bonds can be replaced by: a retro-inverso bonds (C(O)—NH); a reduced amide bond (NH—CH$_2$); a thiomethylene bond (S—CH$_2$ or CH$_2$—S); an oxomethylene bond (O—CH$_2$ or CH$_2$—O); an ethylene bond (CH$_2$—CH$_2$); a thioamide bond (C(S)—NH); a trans-olefine bond (CH=CH); an fluoro substituted trans-olefin bond (CF=CH); a ketomethylene bond (C(O)—CHR) or CHR—C(O) wherein R is H or CH$_3$; and a fluoro-ketomethylene bond (C(O)—CFR or CFR—C(O) wherein R is H or F or CH$_3$.

The polypeptides can be further modified by: acetylation, amidation, biotinylation, cinnamoylation, farnesylation, formylation, myristoylation, palmitoylation, phosphorylation (Ser, Tyr or Thr), stearoylation, succinylation and sulfurylation. The polypeptides of the invention may also be conjugated to, for example, polyethylene glycol (PEG); alkyl groups (e.g., C$_1$-C$_{20}$ straight or branched alkyl groups); fatty acid radicals; and combinations thereof.

Methods of Treatment

The present invention provides for both prophylactic and therapeutic methods of treating a subject at risk of (or susceptible to) a disorder or having a disorder associated with aberrant (e.g., excessive) Notch activity. This is because the polypeptides are expected to act as dominant negative inhibitors of Notch activity. As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small molecules, peptides, antibodies, ribozymes and antisense oligonucleotides.

The polypeptides of the invention can be used to treat, prevent, and/or diagnose cancers and neoplastic conditions. As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states may be categorized as pathologic, i.e., characterizing or constituting a disease state, or may be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include proliferation of cells associated with wound repair.

Examples of cellular proliferative and/or differentiative disorders include cancer, e.g., carcinoma, sarcoma, or metastatic disorders. The compounds (i.e., polypeptides) can act as novel therapeutic agents for controlling breast cancer, T cell cancers and B cell cancer. The polypeptides may also be useful for treating mucoepidermoid carcinoma and medulloblastoma.

Examples of proliferative disorders include hematopoietic neoplastic disorders. As used herein, the term "hematopoietic neoplastic disorders" includes diseases involving hyperplastic/neoplastic cells of hematopoietic origin, e.g., arising from myeloid, lymphoid or erythroid lineages, or precursor cells thereof. Exemplary disorders include: acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) Crit. Rev. in Oncol./Hemotol. 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), multiple mylenoma, hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Examples of cellular proliferative and/or differentiative disorders of the breast include, but are not limited to, proliferative breast disease including, e.g., epithelial hyperplasia, sclerosing adenosis, and small duct papillomas; tumors, e.g., stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

Pharmaceutical Compositions and Routes of Administration

As used herein, the compounds of this invention, including the compounds of formulae described herein, are defined to include pharmaceutically acceptable derivatives or prodrugs thereof. A "pharmaceutically acceptable derivative or prodrug" means any pharmaceutically acceptable salt, ester, salt of an ester, or other derivative of a compound of this invention which, upon administration to a recipient, is capable of providing (directly or indirectly) a compound of this invention. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species. Preferred prodrugs include derivatives where a group which enhances aqueous solubility or active transport through the gut membrane is appended to the structure of formulae described herein.

The compounds of this invention may be modified by appending appropriate functionalities to enhance selective biological properties. Such modifications are known in the art and include those which increase biological penetration into a given biological compartment (e.g., blood, lymphatic system, central nervous system), increase oral availability, increase solubility to allow administration by injection, alter metabolism and alter rate of excretion.

Pharmaceutically acceptable salts of the compounds of this invention include those derived from pharmaceutically acceptable inorganic and organic acids and bases. Examples of suitable acid salts include acetate, adipate, benzoate, benzenesulfonate, butyrate, citrate, digluconate, dodecylsulfate, formate, fumarate, glycolate, hemisulfate, heptanoate, hexanoate, hydrochloride, hydrobromide, hydroiodide, lactate, maleate, malonate, methanesulfonate, 2-naphthalenesulfonate, nicotinate, nitrate, palmoate, phosphate, picrate, pivalate, propionate, salicylate, succinate, sulfate, tartrate, tosylate and undecanoate. Salts derived from appropriate bases include alkali metal (e.g., sodium), alkaline earth metal (e.g., magnesium), ammonium and N-(alkyl)$_4^+$ salts. This invention also envisions the quaternization of any basic nitrogen-containing groups of the compounds disclosed herein. Water or oil-soluble or dispersible products may be obtained by such quaternization.

The compounds of the formulae described herein can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.001 to about 100 mg/kg of body weight, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with the carrier materials to produce a single dosage form will vary depending upon the host treated and the particular mode of administration. A typical preparation will contain from about 5% to about 95% active compound (w/w). Alternatively, such preparations contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained. Patients may, however, require intermittent treatment on a long-term basis upon any recurrence of disease symptoms.

Pharmaceutical compositions of this invention comprise a compound of the formulae described herein or a pharmaceutically acceptable salt thereof; an additional agent including for example, morphine or codeine; and any pharmaceutically acceptable carrier, adjuvant or vehicle. Alternate compositions of this invention comprise a compound of the formulae described herein or a pharmaceutically acceptable salt thereof; and a pharmaceutically acceptable carrier, adjuvant or vehicle. The compositions delineated herein include the compounds of the formulae delineated herein, as well as additional therapeutic agents if present, in amounts effective for achieving a modulation of disease or disease symptoms.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, may also be advantageously used to enhance delivery of compounds of the formulae described herein.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

The pharmaceutical compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

When the compositions of this invention comprise a combination of a compound of the formulae described herein and one or more additional therapeutic or prophylactic agents, both the compound and the additional agent should be present at dosage levels of between about 1 to 100%, and more preferably between about 5 to 95% of the dosage normally administered in a monotherapy regimen. The additional agents may be administered separately, as part of a multiple dose regimen, from the compounds of this invention. Alternatively, those agents may be part of a single dosage form, mixed together with the compounds of this invention in a single composition.

Screening Assays

The invention provides methods (also referred to herein as "screening assays") for identifying polypeptides which modulate the activity of one or more Notch complexes.

The binding affinity of polypeptides to Notch can be measured using the methods described herein, for example, by using a titration binding assay. Notch complex lacking MAML (i.e., a complex of ICN and CSL) be exposed to varying concentrations of a candidate compound (i.e., polypeptide) (e.g., 1 nM, 10 nM, 100 nM, 1 µM, 10 µM, 100 µM, 1 mM, and 10 mM) and binding can be measured using surface plasmon resonance to determine the Kd for binding. Candidate compounds could also be screened for biological activity in vivo, for example, by measuring expression of a Notch responsive reporter in a suitable cell, e.g., in MOLT-4 cells. Cell permeability screening assays in which fluorescently labeled candidate compounds are applied to intact cells, which are then assayed for cellular fluorescence by microscopy or high-throughput cellular fluorescence detection can also be used.

The assays described herein can be performed with individual candidate compounds or can be performed with a plurality of candidate compounds. Where the assays are performed with a plurality of candidate compounds, the assays can be performed using mixtures of candidate compounds or can be run in parallel reactions with each reaction having a single candidate compound. The test compounds or agents can be obtained using any of the numerous approaches in combinatorial library methods known in the art.

Other Applications

A number of embodiments of the invention have been described. Nevertheless, it will be understood that various modifications may be made without departing from the spirit and scope of the invention. Accordingly, other embodiments are within the scope of the following claims.

The invention claimed is:

1. A modified polypeptide of Formula (I),

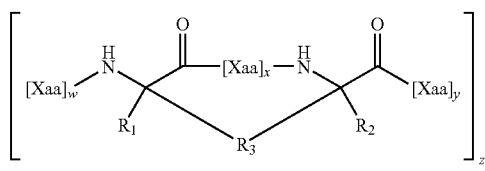

Formula (I)

wherein:

each $R_1$ and $R_2$ are independently H, alkyl, alkenyl, alkynyl, arylalkyl, cycloalkylalkyl, heteroarylalkyl, or heterocyclylalkyl;

each $R_3$ is independently alkyl, alkenyl, alkynyl or $[R_4—K—R_4]_n$; each of which is substituted with 0-6 $R_5$;

each $R_4$ is independently alkyl, alkenyl, or alkynyl;

each $R_5$ is independently halo, alkyl, $OR_6$, $N(R_6)_2$, $SR_6$, $SOR_6$, $SO_2R_6$, $CO_2R_6$, $R_6$, a fluorescent moiety, or a radioisotope;

each K is independently O, S, SO, SO$_2$, CO, CO$_2$, CONR$_6$, or

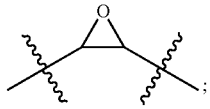 [SMILES: *C1OC1*]

each R$_6$ is independently H, alkyl, or a therapeutic agent;
n is an integer from 1-4;
x is 3, 4 or 6;
y and w are independently an integer between 0 and 15;
z is 1; and
each Xaa is independently an amino acid;
wherein the modified polypeptide consists of 8-20 contiguous amino acids of SEQ ID NO:1 and: (a) within a sequence of 8 contiguous amino acids the side chains of at least one pair of amino acids separated by 3, 4 or 6 amino acids are replaced by the linking group R$_3$ which connects the alpha carbons of the pair of amino acids as depicted in Formula (I); and (b) the alpha carbon of the first of the pair of amino acids is substituted with R$_1$ as depicted in Formula (I) and the alpha carbon of the second of the pair of amino acids is substituted with R$_2$ as depicted in Formula (I); wherein and N or C can be substituted by PEG, spermine, or a carbohydrate.

2. The modified polypeptide of claim 1, wherein y is an integer from 3 to 15.

3. The modified polypeptide of claim 1, wherein R$_1$ and R$_2$ are each independently H or C$_1$-C$_6$ alkyl.

4. The modified polypeptide of claim 1, wherein R$_3$ is a straight chain alkyl, alkenyl, or alkynyl.

5. The modified polypeptide of claim 1 wherein the sequence of [Xaa]$_w$ is LCR.

6. A compound having the formula:

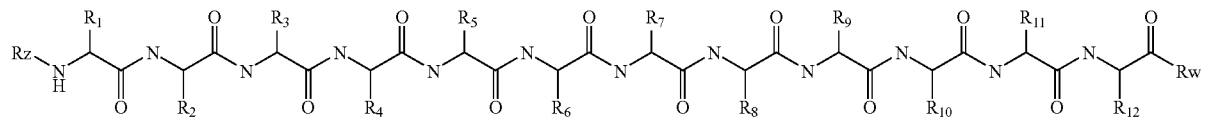

wherein;

R$_1$ is —CH$_2$CH$_2$COOH [E] or —CH$_2$COOH [D] or R$_1$ and R$_8$ together are R$_x$;
R$_2$ is —CH$_2$CH(CH$_3$)$_2$ [L] or —CH$_2$CH$_2$CH$_2$N(H)C(NH)NH$_2$ [R];
R$_3$ is —CH$_2$CH$_2$COOH [E]
R$_4$ is —CH$_2$CH$_2$CH$_2$N(H)C(NH)NH$_2$ [R];
R$_5$ is —CH$_2$CH$_2$C(O)NH$_2$ [Q], —CH$_2$CH$_2$COOH [E], or CH$_2$CH$_2$CH$_2$N(H)C(NH)NH$_2$ [R]; or R$_5$ and R$_9$ together are Ry; or R$_5$ and R$_{12}$ together are Rx;
R$_6$ is —CH$_2$OH [S],

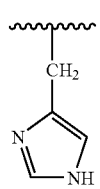

[H] or —CH$_2$COOH [D];
R$_7$ is —C(OH)CH$_3$ [T];
R$_8$ is benzyl [F], —CH$_2$CH(CH$_3$)$_2$ [L], —CH(CH$_3$)$_2$ [V] or R$_1$ and R$_8$ together are R$_x$;
R$_9$ is selected from: —CH$_3$ [A] or —CH$_2$CH$_2$C(O)NH$_2$ [Q] and —CH$_2$OH [S]; or R$_5$ and R$_9$ together are R$_y$;
R$_{10}$ is —CH$_2$CH(CH$_3$)$_2$ [L];
R$_{11}$ is

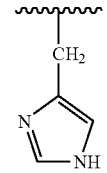

[H], —CH$_2$CH(CH$_3$)$_2$ [L] or

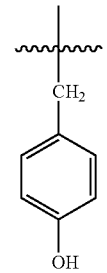

[Y]
R$_{12}$ is —CH$_2$CH$_2$C(O)NH$_2$ [Q] and —CH$_2$OH [S]; or R$_5$ and R$_{12}$ together are R$_x$
provided that when R$_1$ and R$_8$ together are Rx, R$_5$ and R$_9$ are not together Ry and R$_5$ and R$_{12}$ are not together R$_x$;
further provided that when R$_5$ and R$_9$ together are Ry, R$_1$ and R$_5$ are not together R$_x$ and R$_5$ and R$_{12}$ are not together R$_x$;
further provided that when R$_5$ and R$_{12}$ are together R$_x$, R$_5$ and R$_9$ are not together R$_y$ and R$_1$ and R$_8$ are not together R$_x$;
R$_x$ and R$_y$ are each independently alkyl, alkenyl, alkynyl; [R$_{x1}$—K—R$_{x1}$]$_n$; each of which is substituted with 0-6 R$_{x2}$;
R$_{x1}$ is alkyl, alkenyl, or alkynyl;
R$_{x2}$ is halo, alkyl, OR$_{x3}$, N(R$_{x3}$)$_2$, SR$_{x3}$, SOR$_{x3}$, SO$_2$R$_{x3}$, CO$_2$R$_{x3}$, R$_{x3}$, a fluorescent moiety, or a radioisotope;
K is O, S, SO, SO$_2$, CO, CO$_2$, CONR$_{x3}$, or

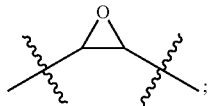

$R_{x3}$ is H, alkyl or a therapeutic agent; and $R_z$ and $R_w$ are independently: H, hydroxyl, an amino acid, 2 to 10 amino acids linked by peptide bonds; tat; or PEG;

n is 3, 4, or 6; and wherein the compound binds a Notch complex with an apparent Kd of less than 1 μM as measured by surface plasmon resonance;

and wherein: a) $R_1$ and $R_8$ together are $R_x$ or b) $R_5$ and $R_9$ together are Ry; or c) $R_5$ and $R_{12}$ together are Rx.

7. The polypeptide of claim 6, wherein $R_1$ and $R_2$ are each independently H or $C_1$-$C_6$ alkyl.

8. The polypeptide of claim 6, wherein the polypeptide is transported through the cell membrane.

9. The polypeptide of claim 1 wherein polypeptide comprises an amino acid sequence selected from SEQ ID NOs:8, 9, 10 and 11, wherein: (a) the side chains of amino acids 8 and 12 are replaced by the linking group $R_3$ which connects the alpha carbons of amino acids 8 and 12 as depicted in Formula (I); and (b) the alpha carbon of amino acid 8 is substituted with $R_1$ as depicted in Formula (I) and the alpha carbon of amino acid 12 is substituted with $R_2$ as depicted in Formula (I).

10. The modified polypeptide of claim 1, wherein the MAML polypeptide consists of SEQ ID NO:8 and: (a) within a sequence of 8 contiguous amino acids the side chains of at least one pair of amino acids separated by 3, 4 or 6 amino acids are replaced by the linking group $R_3$ which connects the alpha carbons of the pair of amino acids as depicted in Formula (I); and (b) the alpha carbon of the first of the pair of amino acids is substituted with $R_1$ as depicted in Formula (I) and the alpha carbon of the second of the pair of amino acids is substituted with $R_2$ as depicted in Formula (I); wherein and N or C can be substituted by PEG, spermine, or a carbohydrate.

11. The modified polypeptide of claim 1, wherein the MAML Polypeptide consists of 8-20 contiguous amino acid of SEQ ID NO:2 and: (a) within a sequence of 8 contiguous amino acids the side chains of at least one pair of amino acids separated by 3, 4 or 6 amino acids are replaced by the linking group $R_3$ which connects the alpha carbons of the pair of amino acids as depicted in Formula (I); and (b) the alpha carbon of the first of the pair of amino acids is substituted with $R_1$ as depicted in Formula (I) and the alpha carbon of the second of the pair of amino acids is substituted with $R_2$ as depicted in Formula (I); wherein and N or C can be substituted by PEG, spermine, or a carbohydrate.

12. A pharmaceutically acceptable salt of the modified polypeptide of Formula (I) of claim 1.

* * * * *

UNITED STATES PATENT AND TRADEMARK OFFICE
CERTIFICATE OF CORRECTION

PATENT NO. : 9,074,009 B2
APPLICATION NO. : 12/478504
DATED : July 7, 2015
INVENTOR(S) : Bradner Page 1 of 1

It is certified that error appears in the above-identified patent and that said Letters Patent is hereby corrected as shown below:

On the title page item [56],

Column 2, Line 3, Other Publications, delete "tumerogenesis," and insert -- tumorigenesis, --, therefor.

Column 2, Line 6, Other Publications, delete "tumerogenesis," and insert -- tumorigenesis, --, therefor.

Column 2, Line 14, Other Publications, delete "1472" and insert -- 1470, --, therefor.

In the claims

Column 50, Line 47, Claim 6, delete "$R_5$" and insert -- $R_8$ --, therefor.

Column 52, Line 11, Claim 11, delete "Polypeptide" and insert -- polypeptide --, therefor.

Signed and Sealed this
Twenty-second Day of December, 2015

Michelle K. Lee
*Director of the United States Patent and Trademark Office*